(12) United States Patent
Rinker et al.

(10) Patent No.: US 10,215,749 B2
(45) Date of Patent: Feb. 26, 2019

(54) PORTED PARALLEL PLATE FLOW CHAMBER AND METHODS FOR USE THEREOF

(71) Applicants: Kristina D. Rinker, Calgary (CA); Robert D. Shepherd, Calgary (CA)

(72) Inventors: Kristina D. Rinker, Calgary (CA); Robert D. Shepherd, Calgary (CA)

(*) Notice: Subject to any disclaimer, the term of this patent is extended or adjusted under 35 U.S.C. 154(b) by 420 days.

(21) Appl. No.: 15/136,169

(22) Filed: Apr. 22, 2016

(65) Prior Publication Data

US 2016/0312172 A1 Oct. 27, 2016

Related U.S. Application Data

(62) Division of application No. 14/212,095, filed on Mar. 14, 2014, now Pat. No. 9,557,320.

(Continued)

(51) Int. Cl.
*G01N 33/50* (2006.01)
*B01L 3/00* (2006.01)
(Continued)

(52) U.S. Cl.
CPC .......... *G01N 33/5023* (2013.01); *B01L 3/502* (2013.01); *B01L 3/5025* (2013.01);
(Continued)

(58) Field of Classification Search
CPC .. B01L 3/502; B01L 3/5025; B01L 2200/027; G01N 33/5023; G01N 33/5064
See application file for complete search history.

(56) References Cited

U.S. PATENT DOCUMENTS

| 7,595,871 B2 | 9/2009 | Weber et al. |
| 2001/0024787 A1 | 9/2001 | Davies et al. |

(Continued)

FOREIGN PATENT DOCUMENTS

| EP | 2972313 B1 | 1/2018 |
| WO | WO 2005/016529 A1 | 2/2005 |
| WO | WO2014143696 | 9/2014 |

OTHER PUBLICATIONS

Communication of the extended European search report for European Patent Application No. 14763559.1 dated Oct. 27, 2016.
(Continued)

*Primary Examiner* — Jill A Warden
*Assistant Examiner* — Dwayne K Handy
(74) *Attorney, Agent, or Firm* — Jenkins, Wilson, Taylor & Hunt, P.A.

(57) ABSTRACT

Flow chambers are provided. In some embodiments, the flow chambers include an inner panel having at least one flow channel having an inlet/outlet opening on each end thereof formed therein, wherein the inlet/outlet openings are adapted to releasably receive a septum; one or more ports adapted to releasably receive a plug and for at least liquid communication with the at least one flow channel, and an outer frame that defines an outer portion of the at least one flow channel and that defines a perimeter of the flow chamber. In some embodiments, the flow chamber has overall dimensions of a standard multiwell plate and the at least one flow channel is located in a position that corresponds to a column location of the standard multiwell plate. Also provided are methods for producing the presently disclosed flow chambers and employing the same to assay biological features of cultured cells and/or tissues.

31 Claims, 15 Drawing Sheets
(1 of 15 Drawing Sheet(s) Filed in Color)

Related U.S. Application Data

(60) Provisional application No. 61/791,770, filed on Mar. 15, 2013.

(51) Int. Cl.
  *C12M 1/34* (2006.01)
  *C12M 1/42* (2006.01)
  *C12Q 1/6876* (2018.01)
  *G01N 33/487* (2006.01)

(52) U.S. Cl.
  CPC ............ *C12M 35/04* (2013.01); *C12M 41/46* (2013.01); *C12Q 1/6876* (2013.01); *G01N 33/487* (2013.01); *G01N 33/5064* (2013.01); *B01L 2200/025* (2013.01); *B01L 2200/026* (2013.01); *B01L 2200/027* (2013.01); *B01L 2200/0689* (2013.01); *B01L 2300/044* (2013.01); *B01L 2300/0609* (2013.01); *B01L 2300/0627* (2013.01); *B01L 2300/0822* (2013.01); *B01L 2300/0829* (2013.01); *B01L 2300/0877* (2013.01); *B01L 2400/0487* (2013.01); *B01L 2400/086* (2013.01); *C12Q 2600/158* (2013.01)

(56) References Cited

U.S. PATENT DOCUMENTS

| | | |
|---|---|---|
| 2003/0157709 A1 | 8/2003 | DiMilla et al. |
| 2004/0029258 A1 | 2/2004 | Heaney et al. |
| 2005/0019231 A1 | 1/2005 | Kahl |
| 2007/0243523 A1 | 10/2007 | Ionescu-Zanetti et al. |
| 2011/0086427 A1 | 4/2011 | Faris et al. |
| 2011/0136162 A1 | 6/2011 | Sun et al. |
| 2014/0274739 A1 | 9/2014 | Rinker et al. |

OTHER PUBLICATIONS

Decision to Grant corresponding to European Patent Application No. 14763559.1 dated Dec. 7, 2017.
Notice of Issuance corresponding to Chinese Patent Application No. 201480026701.0 dated Feb. 22, 2018.
Brown & Larson (2001) Improvements to parallel plate flow chambers to reduce reagent and cellular requirements. BMC Immunol 2(9):1-7.
Communication under Rule 71(3) EPC regarding Intent to Grant corresponding to European Application No. 14763559.1 dated Jul. 25, 2017.
Anderson et al. (2006) The imperative for controlled mechanical stresses in unraveling cellular mechanisms of mechanotransduction. BioMed Eng OnLine 5:27.
Brown & Larson (2001) Improvements to parallel plate flow chambers to reduce reagent and cellular requirements. BMC Immunol 2:9.
Buchanan et al. (1999) Relation between non-uniform hemodynamics and sites of altered permeability and lesion growth at the rabbit aorto-celiac junction. Atherosclerosis 143:27-40.
Burns & DePaola (2005) Flow-conditioned HUVECs suppon clustered leukocyte adhesion by coexpressing ICAM-1 and E-selectin. Am J Physiol Head Circ Physiol 288:H194-H204.
Chatzizisis et al. (2007) Role of endothelial shear stress in the natural history of coronary atherosclerosis and vascular remodeling: molecular, cellular, and vascular behavior. J Am Col Cardiol 49:2379-2393.
Chiu et al. (2007) Mechanisms of induction of endothelial cell E-selectin expression by smooth muscle cells and its inhibition by shear stress. Blood 110:519-528, 2007.
Chung et al., The numerical design of a parallel plate flow chamber for investigation of endothelial cell response to shear stress, Computers & Structures. 200:3. vol. 81. No. 8. pp. 535-546.
Dai et al. (2004) Distinct endothelial phenotypes evoked by arterial waveforms derived from atherosclerosis-susceptible and -resistant regions of human vasculature. Proc Natl Acad Sci USA. 101:14871-14876, 2004.
Dekker et al. (2002) Prolonged fluid shear stress induces a distinct set of endothelial cell genes, most specifically lung Kruppel-like factor (LKLF2). Blood 100:1689-1698.
Duan et al. (2010) Shear stress induced changes of membrane transporter localization and expression in mouse proximal tubule cells. Proc Natl Acad Sci USA 107:21860-21865.
Essig & Friedlander (2003) Tubular shear stress and phenotype of renal proximal tubular cells. J Am Soc Nephrol 14:S33-S35.
Frangos et al. (1985) Flow effects on prostacyclin production by cultured human endothelial cells. Science 227:1477-1479, 1985.
International Search Report Corresponding to International Application No. PCT/US2014/027764 dated Aug. 12, 2014.
LaMack et al. (2005) Interaction of wall shear stress magnitude and gradient in the prediction of arterial macromolecular permeability. Annals Biomed Eng 33:457-464.
McCann et al. (2005) Non-uniform flow behavior in a parallel plate flow chamber alters endothelial cell responses. Ann Biomed Eng 33:328-336.
McKinney et al. (2006) Normal and shear stresses influence the spatial distribution of intracellular adhesion molecule-1 expression in human umbilical vein endothelial cells exposed to sudden expansion flow. J Biomech 39:806-817.
McNeish (2004) Embryonic stem cells in drug discovery. Nature Rev Drug Disc 3:70-80.
Nauman et al. (1999) Quantitative assessment of steady and pulsatile flow fields in a parallel plate flow chamber. Ann Biomed Eng 27:194-199.
Notice of Allowance corresponding to U.S. Appl. No. 14/212,095, dated Dec. 31, 2015.
Notification Concerning Transmittal of International Preliminary Report on Patentability corresponding to International Application No. PCT/US2014/027764 dated Sep. 24, 2015.
Office Action corresponding to U.S. Appl. No. 14/212,095, dated Apr. 20, 2015.
Office Action corresponding to U.S. Appl. No. 14/212,095, dated Jun. 8, 2015.
Rinker et al. (2001) Effect of contact time and force on monocyte adhesion to vascular endothelium. Biophys J 80:1722-1732.
Shah et al. (1997) Liver sinusoidal endothelial cells are responsible for nitric oxide modulation of resistance in the hepatic sinusoids. J Clin Invest 100:2923-2930.
Sheikh et al. (2005) Differing mechanisms of leukocyte recruitment and sensitivity to conditioning by shear stress for endothelial cells treated with tumour necrosis factor-α or interleukin-1β. Br J Pharmacol 145:1052-1061.
Shepherd et al. (2009) Long term shear stress leads to increased phosphorylation of multiple MAPK species in cultured human aortic endothelial cells. Biorheology 46:529-538.
Shepherd et al. (2011) Flow-dependent Smad2 phosphorylation and TGIF nuclear localization in human aortic endothelial cells. Am J Physiol Heart Circ Physiol 301:H98-H107.
Tsai et al. (2007) Laminar fow attenuates intenferon-induced inflammatory responses in endothelial cells. Cardiovasc Res 74:497-505.
Urbich et al. (2001) Upregulation of TRAF-3 by shear stress blocks CD40-mediated endothelial activation. J Clin Invest 108:1451-1458.
Wasserman & Topper (2004) Adaptation of the endothelium to fluid flow: in vitro analyses of gene expression and in vivo implications. Vasc Med 9:35-45.
Yamamoto et al. (2005) Fluid shear stress induces differentiation of Flk-1-positive embryonic stem cells into vascular endothelial cells in vitro. Am J Physiol Heart Circ Physiol 288:H1915-H1924.

110

402

602  604

604  602

604

602

604  602

602

602  604

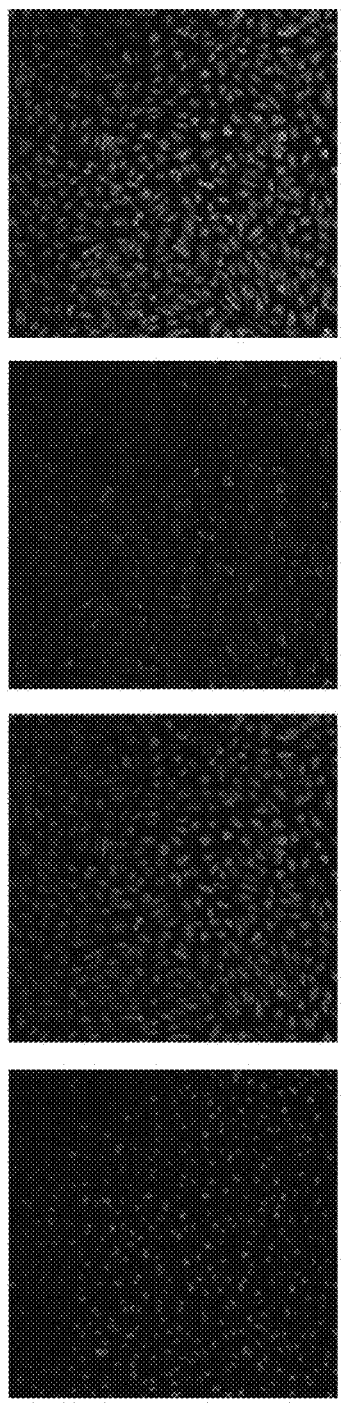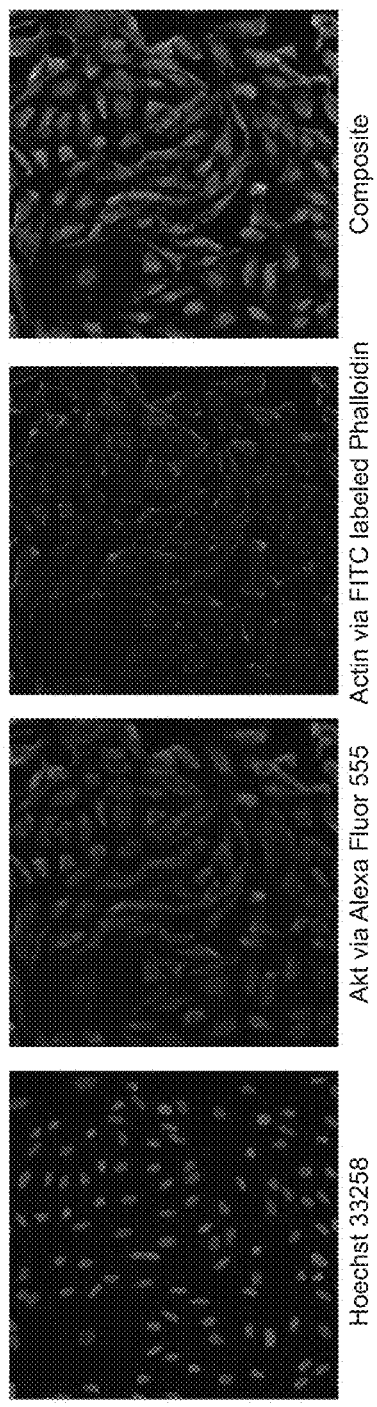
FIG. 12

PORTED PARALLEL PLATE FLOW CHAMBER AND METHODS FOR USE THEREOF

CROSS REFERENCE TO RELATED APPLICATION

The present application is a divisional application of U.S. patent application Ser. No. 14/212,095, filed Mar. 14, 2014, now U.S. Pat. No. 9,557,320, which itself claims the benefit of U.S. Provisional Patent Application Ser. No. 61/791,770, filed Mar. 15, 2013, the disclosure of each of which is incorporated herein by reference in its entirety.

TECHNICAL FIELD

The presently disclosed subject matter relates generally to parallel plate flow chambers and methods for using the same to examine the effects of different fluid flows on cells and biological activities thereof. In particular, the presently disclosed subject matter relates to apparatuses on which cells and/or tissues can be cultured and tested for responses to different fluid flow environments.

BACKGROUND

In vitro cell culture is routinely performed as part of a wide variety of biological research and development programs. In their most common form, cell based experiments are carried out in culture dishes or flasks under static conditions—i.e., those in which no external forces are applied to the cells. Work conducted with statically grown cells has led to many breakthroughs in fields such as cell biology, biochemistry, immunology, and cancer research. However, the inability of static culture to accurately mimic the behavior of cells in dynamic tissue environments constitutes a boundary on the usefulness of this technique. This is illustrated by the number of drug candidates that fail at the transition from in vitro to in vivo testing. It is well known that environmental forces (such as those derived from the flow of blood and other interstitial fluids) influence the behavior of cells and tissues in determining states of health and disease and responses to biochemicals (Buchanan et al., 1999; Urbich et al., 2001; Wasserman & Topper, 2004; Sheikh et al., 2005; Chatzizisis et al., 2007; Chiu et al., 2007; Tsai et al., 2007). Similarly, these forces can also modulate cellular responses to pharmaceuticals, and influence their ultimate efficacy profiles. Since static culture is incapable of introducing variables such as fluid flow into experimental design, alternative means of cell cultivation are necessary to investigate the influence of physiological forces on cell behavior, both in native environments and in response to biochemicals and pharmaceuticals.

The effects of blood flow on cell physiology were first observed in the context of arterial cells susceptible to developing arterial (heart) disease, but other physiological phenomena, such as immune cell recruitment, wound-healing, stem cell differentiation, and tissue regeneration are also known to be force dependent (Rinker et al., 2001; Dekker et al., 2002; Burns & DePaola, 2005; LaMack et al., 2005; Yamamoto et al., 2005; McKinney et al., 2006). Due to the prevalence of heart disease in western society, the effect of fluid flow has become a primary topic of investigation for those interested in understanding its pathology and developing novel treatments. Due to the dependence of the development and progression of heart disease on the characteristics of arterial blood flow, much research is focused upon understanding how various fluid forces influence cell physiology. This work cannot be performed under static conditions, but instead requires the use of dynamic culture systems. Similarly, investigations into the other force dependent physiological processes mentioned above have related culture system requirements. Unfortunately, there has been no commercially available consumable device flexible enough to support the variety of fluid force based cell culture research and development that is being conducted. Instead, most academic and commercial laboratories have created their own systems, while a large number of other entities that would like to perform such experiments do not, as they consider the need to fabricate and assemble the required apparatus as a significant barrier to practice.

In addition to the areas of research and development currently investigated in flow systems, there is a need to expand this approach to the drug discovery pipeline. The same blood vessel cells involved in heart disease serve as gatekeepers for drugs entering the bloodstream, and participate in determining their efficacy (McNeish, 2004; LaMack et al., 2005). Kidney tubular epithelial cells and liver sinusoidal epithelial cells are involved in drug metabolism and excretion, are subject to fluid flow, and their flow sensitivity has been reported (Duan et al., 2010; Essig and Friedlander, 2003; Shah et al., 1997). By conducting initial screening experiments and later toxicity/therapeutic studies with cell cultures exposed to conditions similar to those that exist within the body, results will be more closely linked to actual behavior in tissue, and the economics of the process improved. It is our belief that this can only be achieved through the use of a device such as the chamber device proposed in this application. These outcomes will allow pharmaceutical companies to identify high value candidates earlier, to understand their properties more completely, and to focus their resources on only those molecules that meet the more realistic set of physiological criteria.

There are two common types of devices that support cell and tissue experiments in a dynamic fluid environment. The first of these is the parallel plate flow chamber. Parallel plate flow chambers consist of two parallel plates separated by a gap that forms the flow channel. This gap is generally created by a gasket or spacer that is used to simultaneously seal the flow channel and separate the plates. Fluid is introduced from one end of the chamber and exits on the one opposite. Parallel plate devices are commonly used for exposing cells to defined levels of shear stress, applying specific flow characteristics, and for investigating cell to cell or cell to substrate attachment properties (Frangos et al., 1985; Rinker et al., 2001; McKinney et al., 2006; Shepherd et al., 2009; Shepherd et al., 2011). The other type of device consists of a cone and plate viscometer that has been modified to support cell cultures. In these systems, cells may be exposed to various levels of fluid shear stress and flow waveforms created by the rotation of the cone (Dai et al., 2004). Neither of these systems are currently commercially available for large scale culture activities. Some flow chambers based on a parallel plate design are being marketed by companies such as Ibidi, Fluxion, Cellix, Cellasics, Integrated Biodiagnostics, and Glycotech; however most are based upon small microfluidic flow channels, and do not provide for a wide variety of flow conditions or readout modalities. Additionally, some chambers have issues generating uniform flow (and hence shear stress) distribution (Nauman et al., 1999; Brown & Larson, 2001; McCann et al., 2005; Anderson et al., 2006).

Described herein are flow chambers with differing geometries, obstacles, gap widths, wall heights, etc. designed to provide finely tunable flow conditions, as well as methods of making and using the same to assay various biological properties of cells and/or tissues experiencing different flow conditions.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides in some embodiments a flow chamber. In some embodiments, the flow chamber comprises (a) an inner panel having at least one flow channel formed therein, wherein the at least one flow channel has an inlet/outlet opening on each end thereof, and further wherein the inlet/outlet openings are adapted to releasably receive a septum; (b) one or more ports adapted for at least liquid communication with the at least one flow channel to permit liquid or and/or a reagent to be added the at least one flow channel, said ports adapted to releasably receive a plug, and optionally wherein the one or more ports are adapted to provide a liquid-proof seal to the at least one flow channel, and further optionally wherein the ports are adapted to be resealable; and (c) an outer frame that defines an outer portion of the at least one flow channel and that defines a perimeter of the flow chamber. In some embodiments, the inlet/outlet openings comprise a recess adapted to receive the septum. In some embodiments, the outer frame comprises a surface upon which cells can be grown in culture. In some embodiments, the presently disclosed flow chamber comprises two or more flow channels, optionally three, four, five, six, seven, eight, nine, ten, eleven, twelve, or more flow channels.

In some embodiments, the flow chamber has overall dimensions of a standard 6, 12, 24, 48, 96, 384, or 1024 well multiwell plate and the at least one flow channel is located in a position that corresponds to a column location of a standard 6, 12, 24, 48, 96, 384, or 1024 well multiwell plate. In some embodiments, the flow chamber has the overall dimensions of a standard multiwell plate such as a standard 96 well or 384 well multiwell plate, and each of a series of virtual wells is present in a location aligned with a well position of a standard multiwell plate such as a standard 96 well or 384 well multiwell plate. In some embodiments, the presently disclosed flow chamber comprises two, three, four, five, six, seven, eight, or up to 12 flow channels, each of which is individually located in a column position that corresponds to a different column location of a standard 96 well plate. In some embodiments, the overall dimensions of the flow chamber are consistent with ANSI/SBS multiwell plate standards such as ANSI/SBS 96 or 384 well multiwell plate standards.

In some embodiments, the at least one flow channel has dimensions of between about 5 and 80 mm long by about 1 and 20 mm wide by about 0.025 and 2.5 mm high. In some embodiments, the at least one flow channel is characterized by one or more gaps, obstacles, and/or other modifications designed to create one or more variable fluid dynamic conditions within the at least one flow channel. In some embodiments, the at least one flow channel has an increasing flow channel height along at least a portion of its length. In some embodiments, the flow channel height increases in a plurality of steps.

In some embodiments, at least an inner surface of the at least one flow channel is chemically and/or physically treated and/or is functionalized by reactive groups and/or by macromolecules.

In some embodiments, the presently disclosed flow chamber comprises a septum adapted for placement in one of the inlet/outlet openings. In some embodiments, the septum is adapted to be liquid tight when the first inlet/outlet opening, the second inlet/outlet opening, or both are in fluid communication with the at least one flow channel. In some embodiments, each inlet opening, each outlet opening, or all inlet/outlet openings comprise a septum placed therein.

In some embodiments, at least one of the one or more ports comprises fitted therein a polymer plug, optionally a gas permeable plug. In some embodiments, the one or more ports comprise one or more hydrophobic polymer plugs, optionally one or more hydrophobic porous or non-porous polymer plugs. In some embodiments, the one or more hydrophobic polymer plugs are self-sealing, optionally self-sealing within a port. In some embodiments, the one or more ports comprise one or more plugs adapted to accept a standard pipettor shaft, a standard micropipettor shaft, an automated liquid handler head or tip, or any combination thereof. In some embodiments, the one or more ports comprise one or more plugs that are hollow. In some embodiments, the one or more plugs are adapted for connection to one or more gas filters, optionally wherein the one or more gas filters has a porosity of at most 0.2 µm.

In some embodiments, the inner panel, the outer frame, or both comprise one or more view windows through which the at least one flow channel or a cell growing thereupon can be observed. In some embodiments, the presently disclosed flow chamber further comprises one or more viewing windows positioned within the perimeter defined by the skirt and between the welding ribs. In some embodiments, the one or more viewing windows are located above or below a flow channel, optionally over or under the entire length of a flow channel. In some embodiments, the one or more viewing windows are characterized by a thinner wall in the outer frame or inner panel than is present in the outer frame or inner panel at positions other than directly under or over the flow channel. In some embodiments, the inner panel, the outer frame, the one or more view windows, or any combination thereof are made from one or more plastics that are non-birefringent, non-auto-fluorescent, or both. In some embodiments, the outer frame comprises bottom viewing windows that are made of glass.

In some embodiments, the outer frame comprises a skirt defining a perimeter and welding ribs positioned along the bottom of the flow chamber. In some embodiments, the outer frame (i) is adapted to seal the septum in its corresponding inlet/outlet opening; and/or (ii) comprises one or more holes to access the septum for fluidics connections.

In some embodiments, the flow chamber is adapted for sealing by ultrasonic welding of the inner panel and the outer frame.

In some embodiments, the inner panel and the outer frame are produced by injection molding.

In some embodiments, the flow chamber of the presently disclosed subject matter is provided as a preassembled, presterilized, liquid tight, and tissue culture ready device.

In some embodiments, the flow chamber of the presently disclosed subject matter further comprises at least a first liquid reservoir that is in fluid communication with the at least one flow channel via a first line attached to the first inlet/outlet opening. In some embodiments, the first liquid reservoir is contained within the flow chamber device.

The presently disclosed subject matter also provides a flow chamber comprising (a) an inner panel having at least one flow channel formed therein, wherein the at least one flow channel has an inlet/outlet opening on each end thereof, and further wherein the inlet/outlet openings are adapted to releasably receive a septum; (b) one or more ports adapted for at least liquid communication with the at least one flow channel to permit liquid or and/or a reagent to be added the at least one flow channel; and (c) an outer frame that defines an outer portion of the at least one flow channel and that defines a perimeter of the flow chamber; wherein (i) the outer frame has a footprint equivalent to that of a standard multiwell plate such as a standard 96 well or 384 well multiwell plate; (ii) each of the at least one flow channels is located in a position that corresponds to a column location of a standard multiwell plate such as a standard 96 well or 384 well multiwell plate; and (iii) each of the at least one flow channels comprises a plurality of virtual wells, each virtual well is located in a position that corresponds to a well location of a standard multiwell plate such as a standard 96 well or 384 well multiwell plate. In some embodiments, the presently disclosed flow chamber further comprises one or more contact points adapted to facilitate interaction of the flow chamber with an automated plate handling apparatus, a multiwell plate reader, an automated microscopy system or any combination thereof. In some embodiments, the inner panel comprises a surface upon which cells can be grown in culture. In some embodiments, the flow chamber of the presently disclosed subject matter comprises one, two, three, four, six, or twelve flow channels.

The presently disclosed subject matter also provides methods for producing the presently disclosed flow chambers. In some embodiments, the methods comprise assembling the inner panel and the outer frame of any embodiment of the presently disclosed flow chambers and ultrasonically welding the inner panel to the outer frame, optionally via welding ribs positioned along the bottom of the flow chamber.

The presently disclosed subject matter also provides methods for assaying biological feature of cultured cells and/or tissues. In some embodiments, the assaying is done in the presence of treatment materials including but not limited to small organic molecules, biochemicals, and the like. In some embodiments, the assaying is done in the absence of treatment materials including but not limited to small organic molecules, biochemicals, and the like. In some embodiments, the presently disclosed methods comprise (a) growing a cultured cell or tissue on a growth surface present in a flow chamber of the presently disclosed subject matter; (b) applying a first flow condition and/or treatment materials to the cultured cell or tissue; and (c) assaying a biological feature of the cultured cell or tissue under the first flow condition to produce a first analysis of the biological feature of the cultured cell or tissue under the first flow condition with or without treatment materials. In some embodiments, the biological feature comprises a growth rate, an apoptosis or death rate, a morphology, and/or an expression profile of one or more gene products in the cultured cell or tissue before, after, and/or during application of the first flow condition. In some embodiments, the assaying comprises generating a gene expression profile of one or more genes in the cultured cell or tissue before, after, and/or during application of the first flow condition.

In some embodiments, the presently disclosed methods further comprise applying a second flow condition with or without treatment materials to the cultured cell or tissue before and/or after application of the first flow condition. In some embodiments, the first flow condition and the second flow condition are different. In some embodiments, the first flow condition or the second flow condition comprises a static flow condition.

In some embodiments, the presently disclosed methods further comprise assaying the biological feature of the cultured cell or tissue subsequent to and/or while applying the second flow condition to produce a second analysis of the biological feature of the cultured cell or tissue under the second flow condition, with or without treatment materials. In some embodiments, the biological feature comprises gene expression levels of one or more genes in the cultured cell or tissue. In some embodiments, the presently disclosed methods further comprise comparing the first analysis to the second analysis in order to identify differences in a response of the cultured cell or tissue to the first flow condition as compared to the second flow condition, with or without treatment materials. In some embodiments, the biological feature comprises gene expression levels of one or more genes in the cultured cell or tissue and the comparing step identifies at least one gene for which expression differs under the first flow condition as compared to the second flow condition (alternatively with or without treatment materials) by at least two-fold.

It is thus an object of the presently disclosed subject matter to provide a flow chamber.

An object of the presently disclosed subject matter having been stated hereinabove, and which is achieved in whole or in part by the presently disclosed subject matter, other objects will become evident as the description proceeds when taken in connection with the accompanying Figures and non-limiting examples as best described herein below.

BRIEF DESCRIPTION OF THE FIGURES

The patent or application file contains at least one drawing executed in color. Copies of this patent or patent application publication with color drawing(s) will be provided by the Office upon request and payment of the necessary fee.

Exemplary embodiments of the subject matter described herein will now be explained with reference to the accompanying Figures, wherein like numerals represent like parts, of which:

FIG. 12 presents a series of multichannel fluorescence microscopy images of cells grown on 1.2 mm thick polystyrene labeled for Akt and F-actin fiber distribution. Magnifications of 20× and 40× are shown.

DETAILED DESCRIPTION

Figure 1:
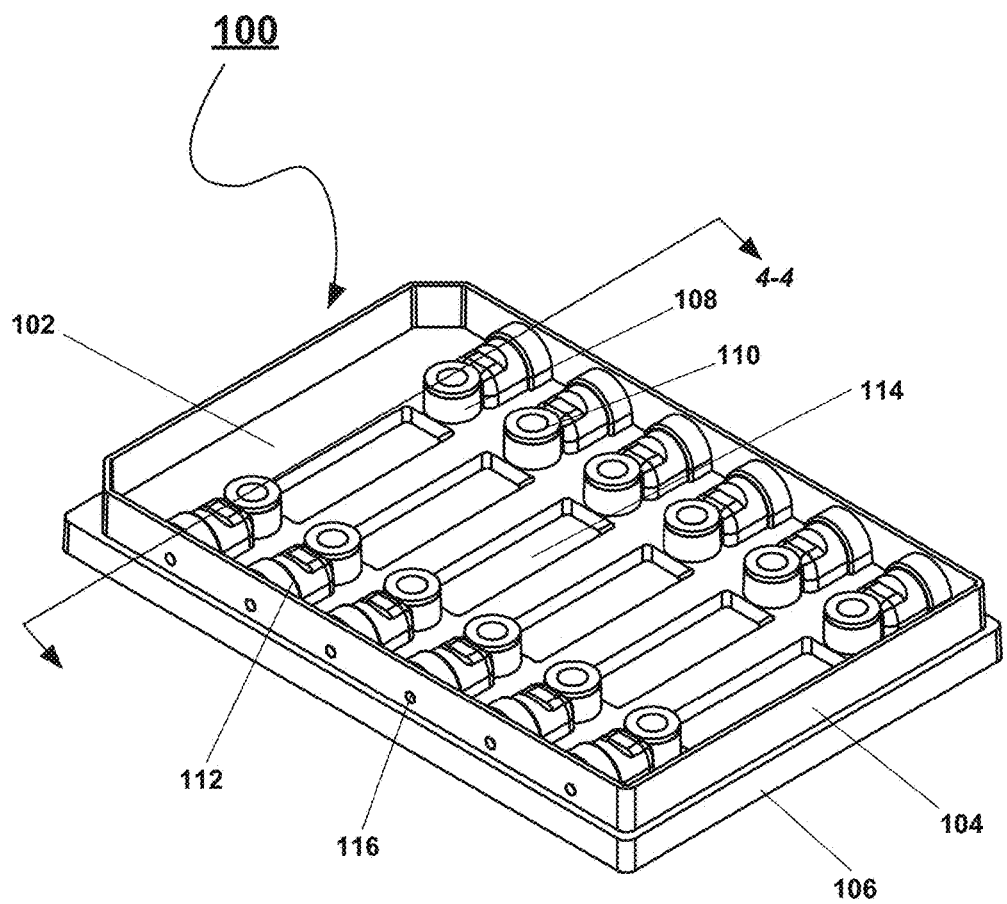
FIG. 1 is a perspective view of an exemplary flow chamber 100 of the presently disclosed subject matter.
Figure 2:
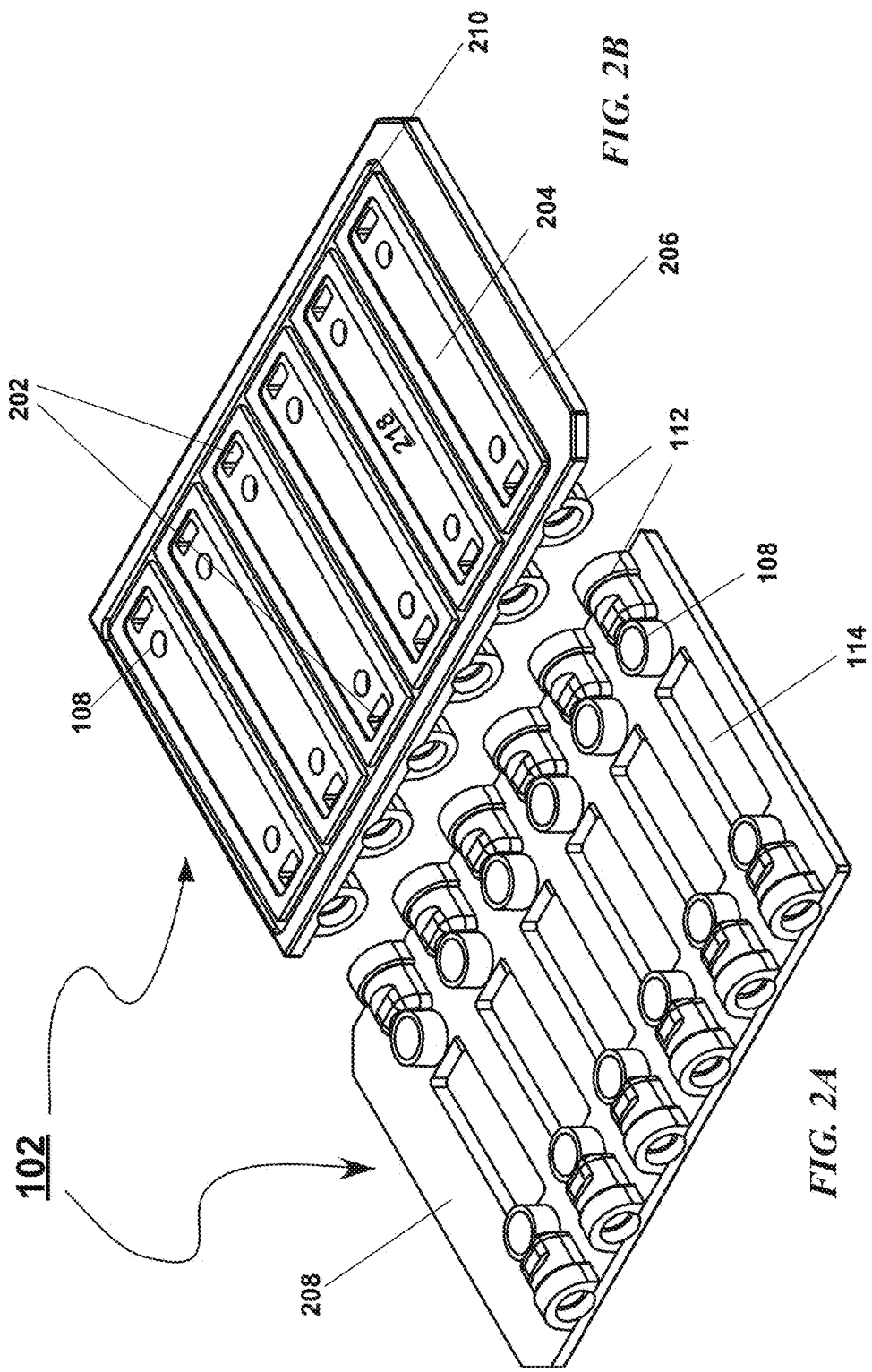
FIGS. 2A and 2B are a top view and a bottom view, respectively, of exemplary inner panel 102 of the presently disclosed subject matter.
Figure 3:
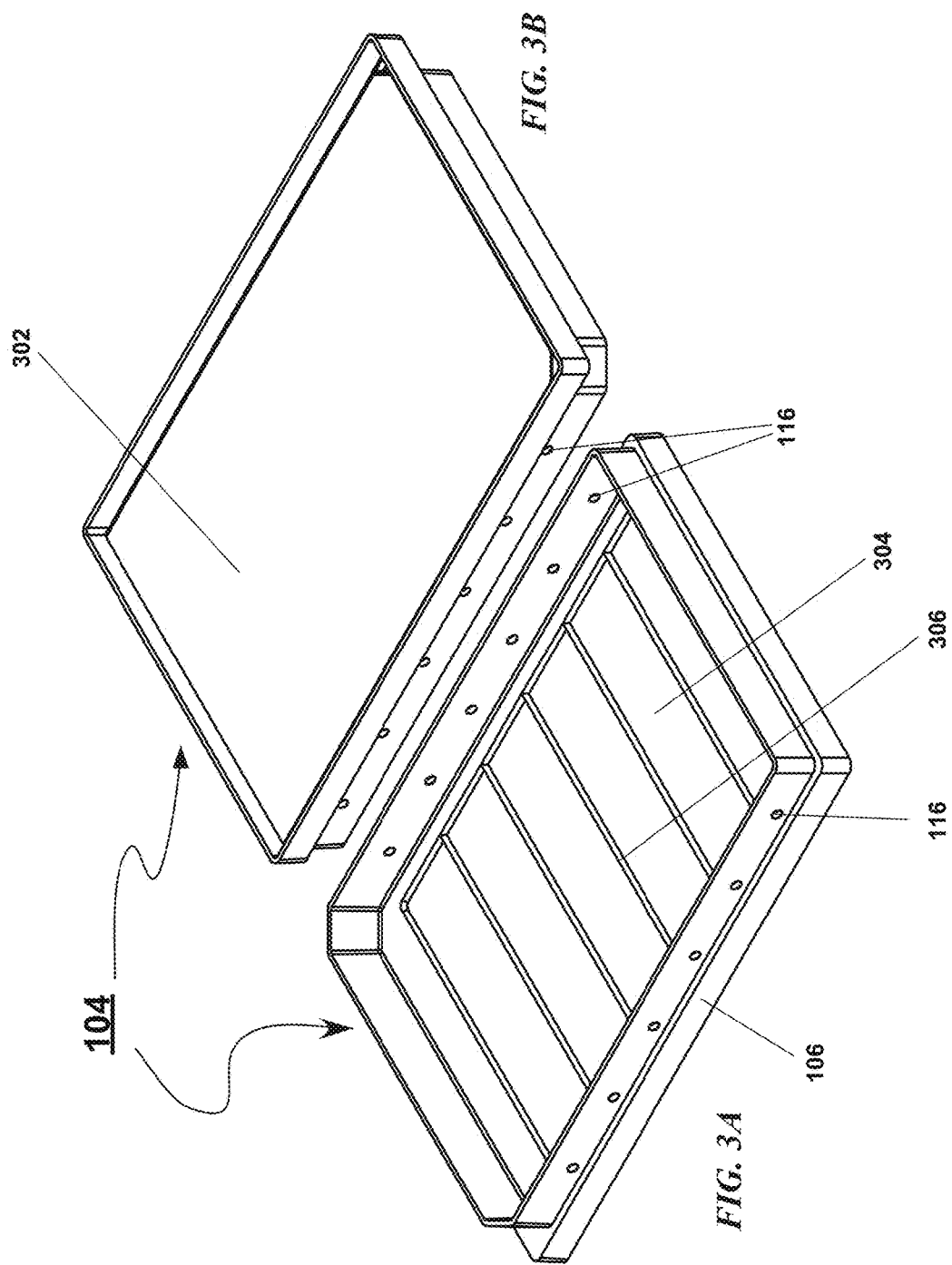
FIGS. 3A and 3B are a top view and a bottom view, respectively, of exemplary outer frame 104 of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

All references listed herein, including but not limited to patents, patent application publications, journal articles, and database entries (e.g., GENBANK® database entries, including all annotations and references cited therein) are incorporated herein by reference to the extent that they supplement, explain, provide a background for, or teach methodology, techniques, and/or compositions employed herein.

Following long-standing patent law convention, the terms "a", "an", and "the" mean "one or more" when used in this application, including the claims. Thus, the phrase "a flow channel" refers to one or more flow channels, unless the context clearly indicates otherwise.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include the use of either of the other two terms.

The term "about", as used herein when referring to a measurable value such as an amount of weight, time, dimension, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods and/or to employ the presently disclosed flow chambers.

Reference will now be made in detail to the description of the present subject matter, one or more examples of which are shown in the Figures. Each example is provided to explain the subject matter and not as a limitation. In fact, features illustrated or described as part of one embodiment can be used in another embodiment to yield still a further embodiment. It is intended that the present subject matter cover such modifications and variations. Wherever possible, the same reference numbers will be used throughout the Figures to refer to the same or like parts. The scaling of the Figures does not represent precise dimensions of the various elements illustrated therein.

Referring now to the Figures, again wherein like reference numerals refer to like parts throughout when possible, a flow chamber in accordance with one embodiment of the presently disclosed subject matter is referred to generally at 100. Referring in particular to FIGS. 1-4, flow chamber 100 includes inner panel 102 and outer frame 104. In some embodiments, the thickness of inner panel 102 and outer frame 104 is in the range of about 0.1 to about 1.0 mm, optionally about 0.9 mm. Outer frame 104 includes a skirt 106 that defines the perimeter of flow chamber 100 and also includes a bottom section 302, best seen in FIGS. 3B and 4. Inner panel 102 comprises a recess 204 in a lower surface 206 thereof and a top view window 114 defined in an upper surface 208 thereof. Outer frame 104 includes fluidics holes 116 which are adapted for placement for communication with septa holders 112 in inner panel 102 when inner panel 102 and outer frame 104 are assembled. Inner panel 102 thus includes septa holders 112, which are adapted to receive septa 402. Inner panel 102 and outer frame 104 define a flow channel 404 wherein an inner portion of flow channel 404 is defined by recess 204 in inner panel 102 and an outer portion of flow channel 404 is defined by surface 304 of bottom section 302 of outer frame 104. In some embodiments, flow channel 404 has dimensions of between about 5 and 80 mm long by about 1 and 20 mm wide by about 0.025 and 2.5 mm high. In some embodiments, the width of flow channel 404 is about 10 mm, its length is about 60 mm, and its height is about 0.40 mm. Ports 108 are formed in inner panel 102 and permit gas or other exchange with flow channel 404. Ports 108 can be releasably sealed with plugs 110. In some embodiments, plug 110 can comprise a hydrophobic material, optionally a hydrophobic porous material, a gas permeable material, or other material as described elsewhere herein. In some embodiments, plug 110 can be self-sealing. In some embodiments, plug 110 can be adapted to fit onto an end of a standard 1000 µl, 200 µl, or 20 µl pipettor shaft, and/or an automated liquid handler head or tip. In some embodiments, plug 110 can be hollow and connected to a filter, optionally a gas filter, which in some embodiments has a porosity of at most 0.2 µm porosity for gas exchange.

Figure 4:
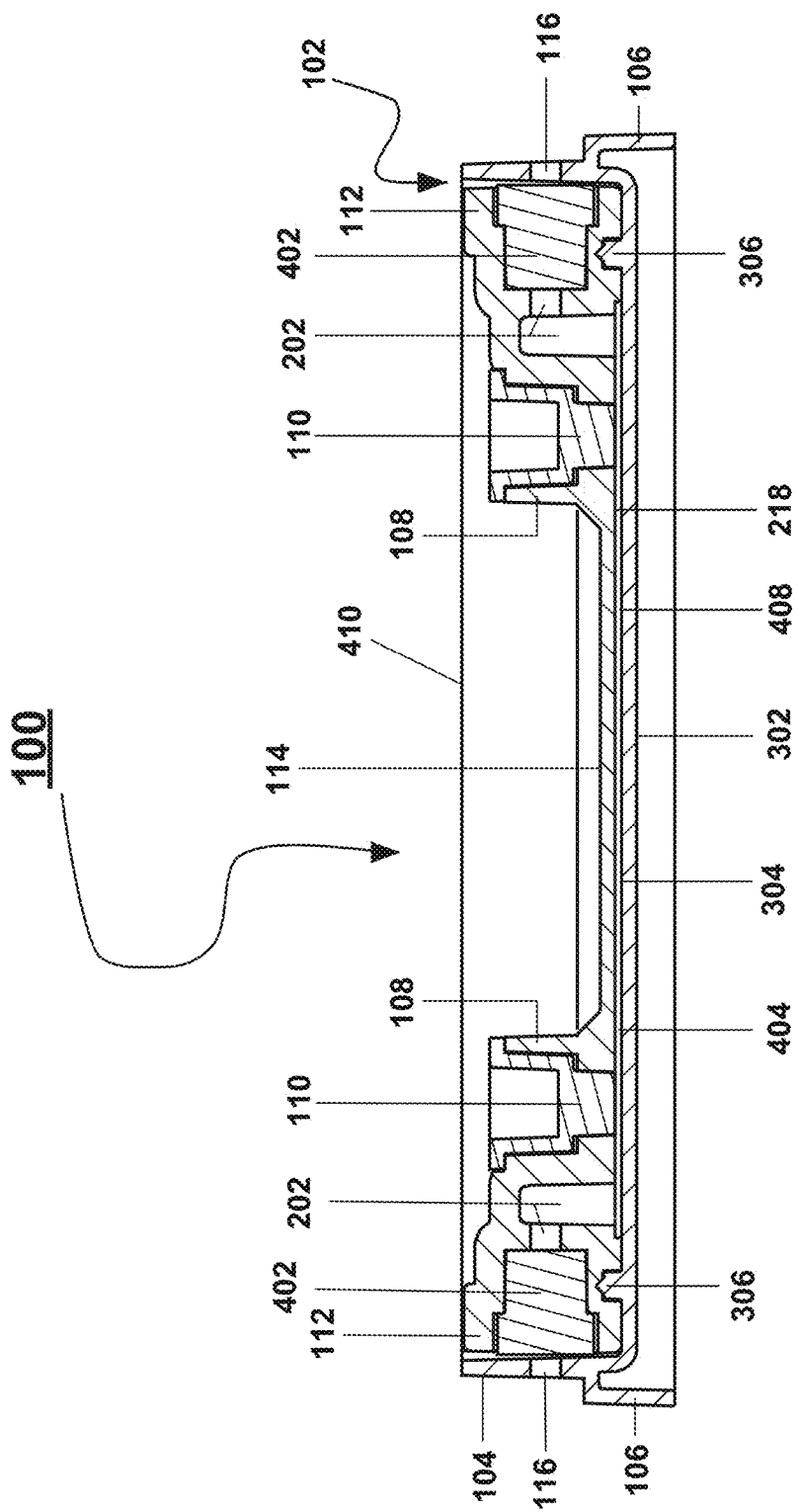
FIG. 4 is a cross sectional view along the line 4-4 in FIG. 1 of an exemplary flow chamber 100 of the presently disclosed subject matter.
Figure 5A:
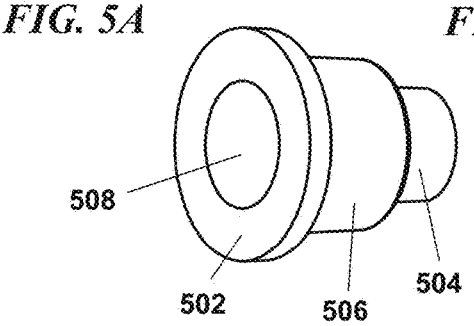
FIGS. 5A-5H are perspective views of an exemplary plug 110 of the presently disclosed subject matter.
Figure 5B:
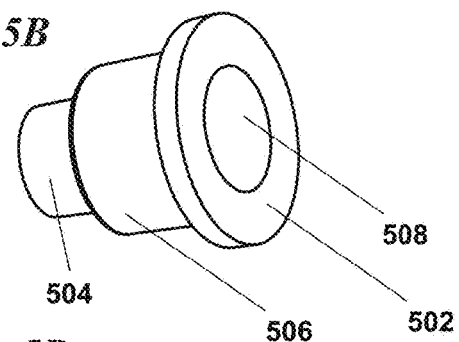
Figure 5C:
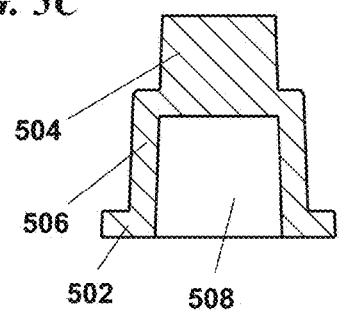
Figure 5D:
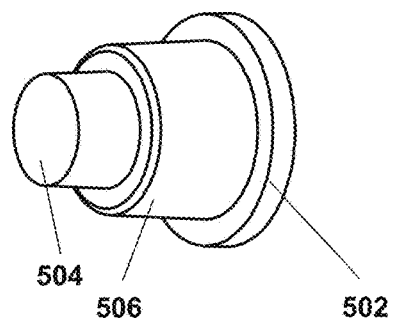
Figure 5E:
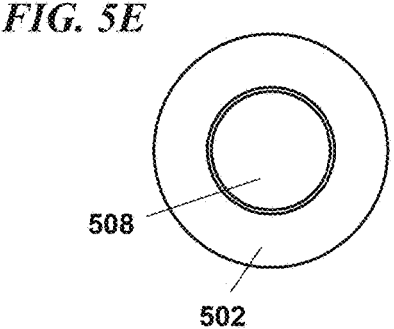
Figure 5F:
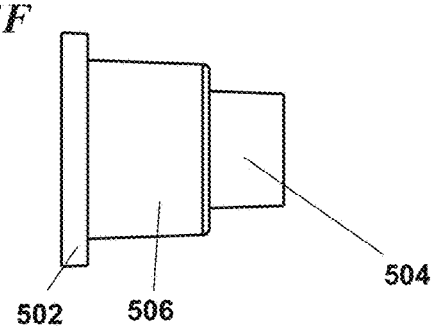
Figure 5G:
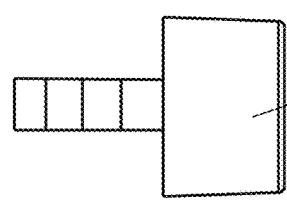
Figure 5H:
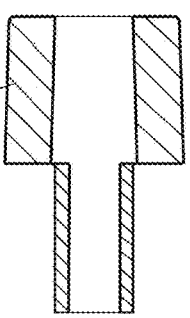
Figure 6A:
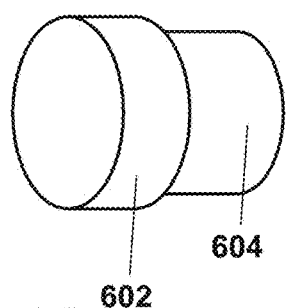
FIGS. 6A-6F are perspective views of an exemplary septum 402 of the presently disclosed subject matter.
Figure 6B:
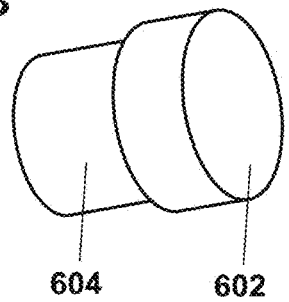
Figure 6C:
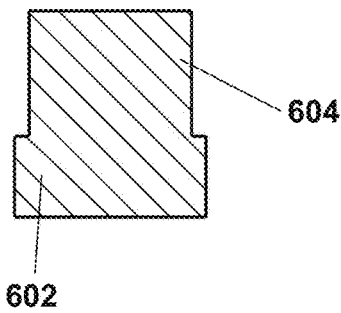
Figure 6D:
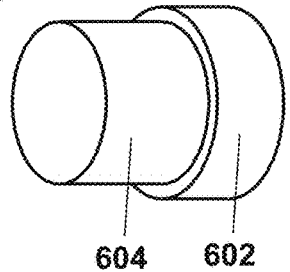
Figure 6E:
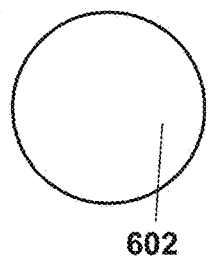
Figure 6F:
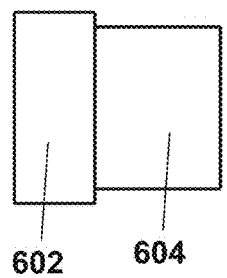

Continuing with reference to FIGS. 1-4, top view window 114 and bottom section 302 can comprise a material through which flow channel 404 can be observed, such as but not limited to one or more non-birefringent and/or non-auto-fluorescent plastics. In some embodiments, a non-birefringent and/or non-auto-fluorescent plastic is polystyrene. In some embodiments, bottom section 302 can be thinner at positions over flow channel 404 as compared to other positions. In some embodiments, bottom section 302 can be made from glass and/or contain a section that comprises glass. Flow channel 404 includes a growth surface 408, wherein cell growth or other activity in flow channel 404 is observed. In some embodiments, surface 304 and growth surface 408 are the same surface when flow chamber 100 is assembled. Inner panel 102 further comprises flow channel inlet/outlet 202 which provides for communication and connection between fluidics holes 116, septum 402 and flow channel 404. In some embodiments, flow channel inlet/outlet 202 acts as a bubble trap. Further, inner panel 102 comprises a groove 210 adapted to receive welding rib 306 on outer frame 104 when outer frame 104 and inner panel 102 are assembled. When presented as an assembled unit, as shown in FIGS. 1 and 4, flow chamber 100 thus includes inner panel 102 attached to outer frame 104 via welding rib 306. Welding can be accomplished via an ultrasonic welding approach or by any other approach that might be apparent to one of ordinary skill in the art upon a review of the instant disclosure. Before welding occurs, septa 402 are installed in septa holders 112 such that fluidics holes 116 are aligned with the center of septa 402. Outer frame 104 seals septa 402 into septa holder 112. Septa 402 are adapted to be liquid tight in an assembled flow chamber 100, including when flow channel inlet/outlets 202 are in fluid communication with flow channel 404. Flow channel inlet/outlets 202 can also serve as a bubble trap to capture gas bubbles in entering fluid prior to contact with the flow channel 404. Further, septa 402 receive fluidics connections from a reservoir (not shown in FIGS. 1 through 4) by being pierced with, for example a needle or other small tube, to introduce or remove flow from flow chamber 100. Indeed, fluid flow can be accomplished from one fluidics hole 116 as an inlet to an opposed fluidics hole 116 that can serve as an outlet. In some embodiments, septa 402 create a liquid tight seal around a line used to introduce flow into flow chamber 100.

Referring now to FIGS. 5A-5H, a plug 110 in accordance with the presently disclosed subject matter is shown in more detail. Plug 110 can comprise a flange 502, a post 504, and a stopper 506. Void space 508 is also defined in the interior of plug 110. Plug 110 is adapted to releasably seal port 108 particularly via stopper 506. Plug 110 is further adapted to retain liquid within flow chamber 100 until purposefully removed. In some embodiments, plug 110 can be adapted to fit onto an end of a standard 1000 µl, 200 µl, or 20 µl pipettor shaft, or an automated liquid handler head or tip, via void space 508. In some embodiments, plug 110 can be self-sealing. In other embodiments, plug 110 can be porous, or porous and self-sealing. In some embodiments, plug 110 can be connected to a filter, optionally a gas filter, which in some embodiments has a porosity of at most 0.2 µm porosity for gas exchange.

Referring now to FIGS. 6A-6F, a septum 402 in accordance with the presently disclosed subject matter is shown in more detail. Septum 402 can comprise a head 602 and a post 604. The center of septum 402 is aligned with fluidics hole 116 and flow channel inlet/outlet 202 to provide for the flow of fluid into the flow channel 404. Septum 402 is elastomeric, and adapted to create a liquid tight seal to retain liquid within flow chamber 100 until purposefully removed.

Figure 7A:
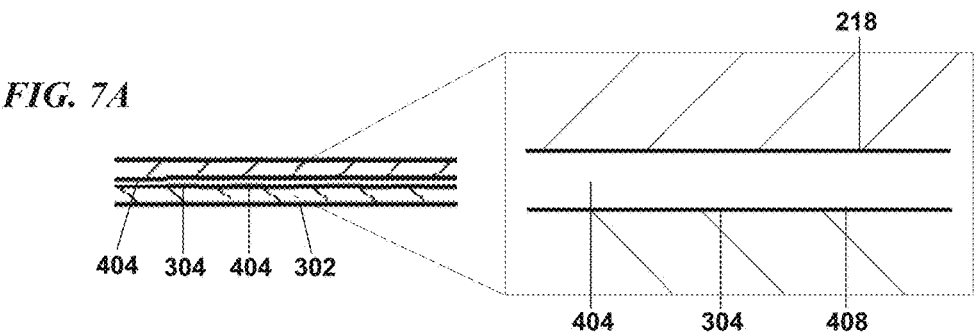
FIGS. 7A-7D are schematic sectional views of an exemplary growth surface 408 of the presently disclosed subject matter showing exemplary different geometries, obstacles, gap widths, and wall heights respectively.
Figure 7B:
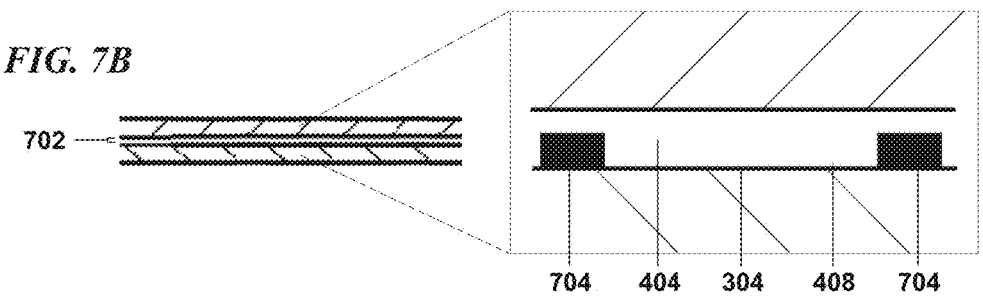
Figure 7C:
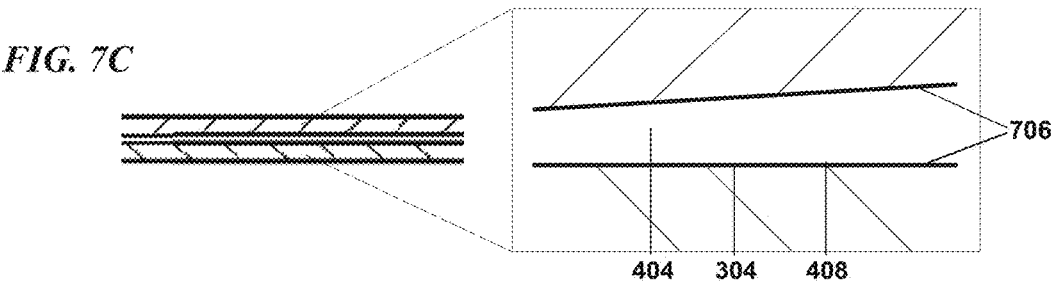
Figure 7D:
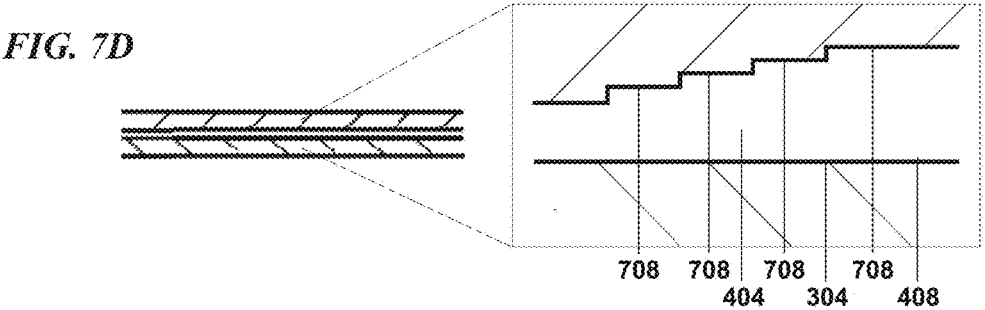

Referring now to FIGS. 7A-7C, certain features of flow channel 404 are depicted. Particularly, flow channel 404 can comprise one or more gaps, obstacles, and/or other modifications designed to create one or more variable fluid dynamic conditions within flow channel 404. As shown in FIG. 7A with a heavy black line, flow channel 404 can include modified upper surface 218 and/or surface 304 of flow chamber 404. Representative modifications include but are not limited to chemical and/or physical treatments and/or functionalization by reactive groups and/or by macromolecules. As best seen in FIG. 7B, flow channel 404 can include obstacles 704 that can be of any geometric shape or combination of shapes, and can be placed in gap 702 between recess 204 in inner panel 102 and surface 304. Further, as best seen in FIG. 7C, a variable gap 706 between recess 204 in inner panel 102 and surface 304 is provided so that the height of flow channel 404 can vary, for example, can increase, for at least a portion of its length. As shown in FIG. 7D, the height of the walls of flow channel 404 can vary, for example increase, in a plurality of steps 708.

Figure 8:
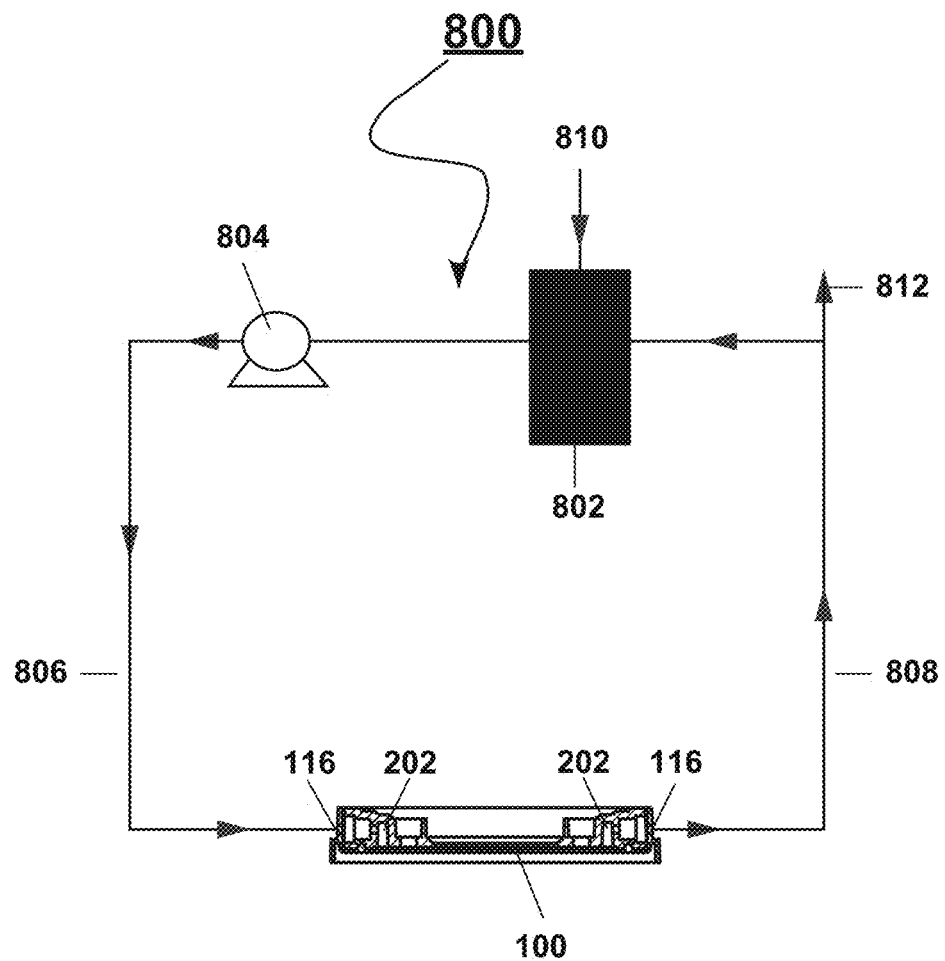
FIG. 8 is a schematic of an exemplary flow chamber of the presently disclosed subject matter connected to a flow channel.

Referring now to FIG. 8, a flow loop 800 including flow chamber 100 of the presently disclosed subject matter is provided. A pump 804 delivers fluid from liquid reservoir 802 via first fluid line 806 to flow chamber 100 via fluidics hole 116. Fluid is introduced to flow chamber 100 through septa 402 (not shown) and flows through flow channel inlet/outlet 202 through flow channel 404 (not shown) and out opposite flow channel inlet/outlet 202 via septa 402 (not shown) and fluidics hole 116 to second fluid line 808. Appropriate liquid levels are maintained in liquid reservoir 802 via liquid feed line 810, and control of other operating parameters can also be included, for example system pressure, gas exchange, or pH. The direction of the flow is indicated by arrows in FIG. 8, and spent fluid is collected, if desired, for appropriate processing at arrowhead 812. While a representative configuration is provided in FIG. 8, any suitable flow direction or configuration is provided in accordance with the presently disclosed subject matter as would be apparent to one of ordinary skill in the art upon review of the present disclosure, including but not limited to inclusion of the fluid reservoir within the boundaries of the flow chamber 100.

Figure 9A:
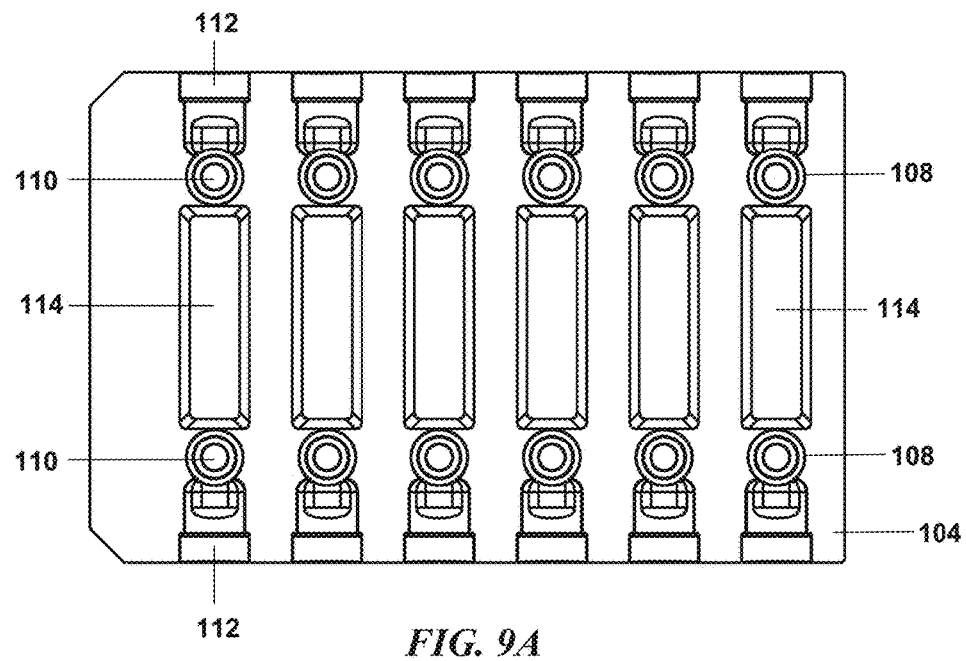
FIGS. 9A and 9B are top views of exemplary inner panel 102 of the presently disclosed subject matter.
Figure 9B:
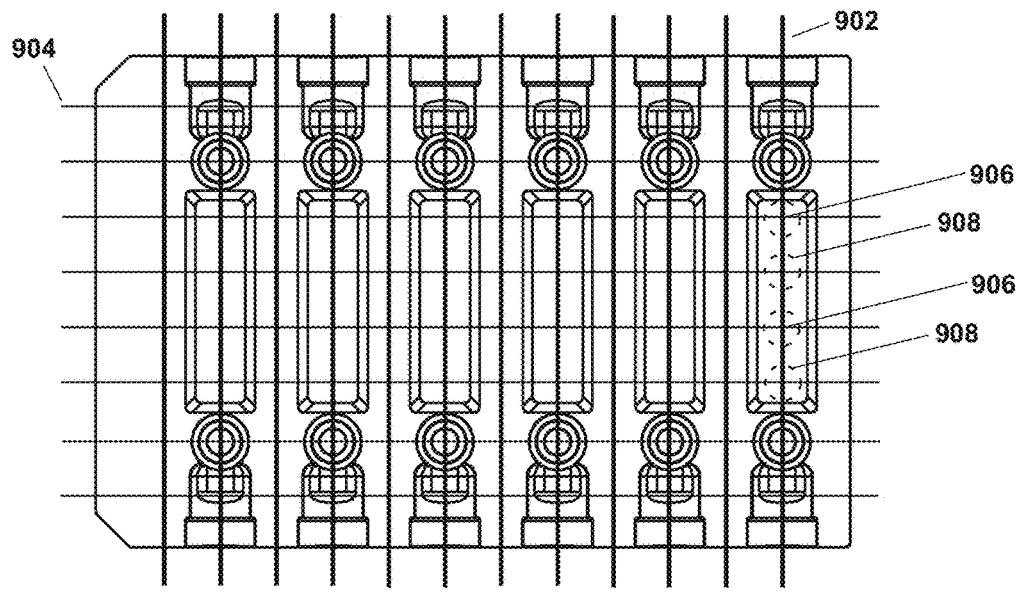
Figure 10A:
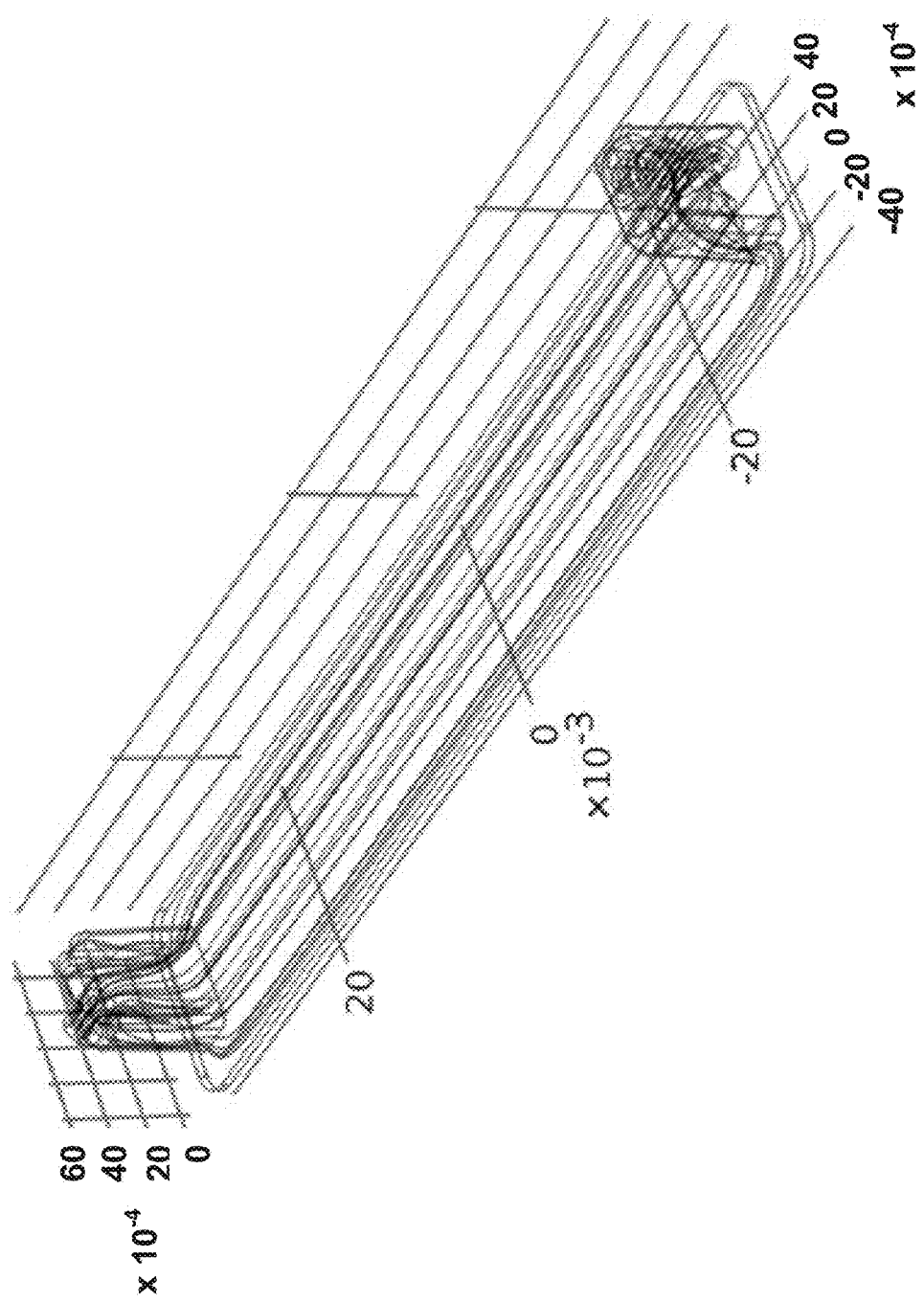
FIGS. 10A-10D are computational fluid dynamic model renderings of fluid streamlines for two viscosities and constant shear stress along a preferred flow channel growth surface.
Figure 10B:
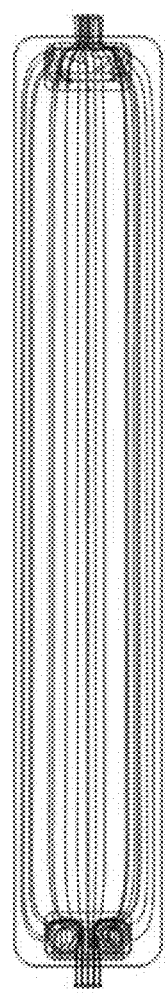
Figure 10C:
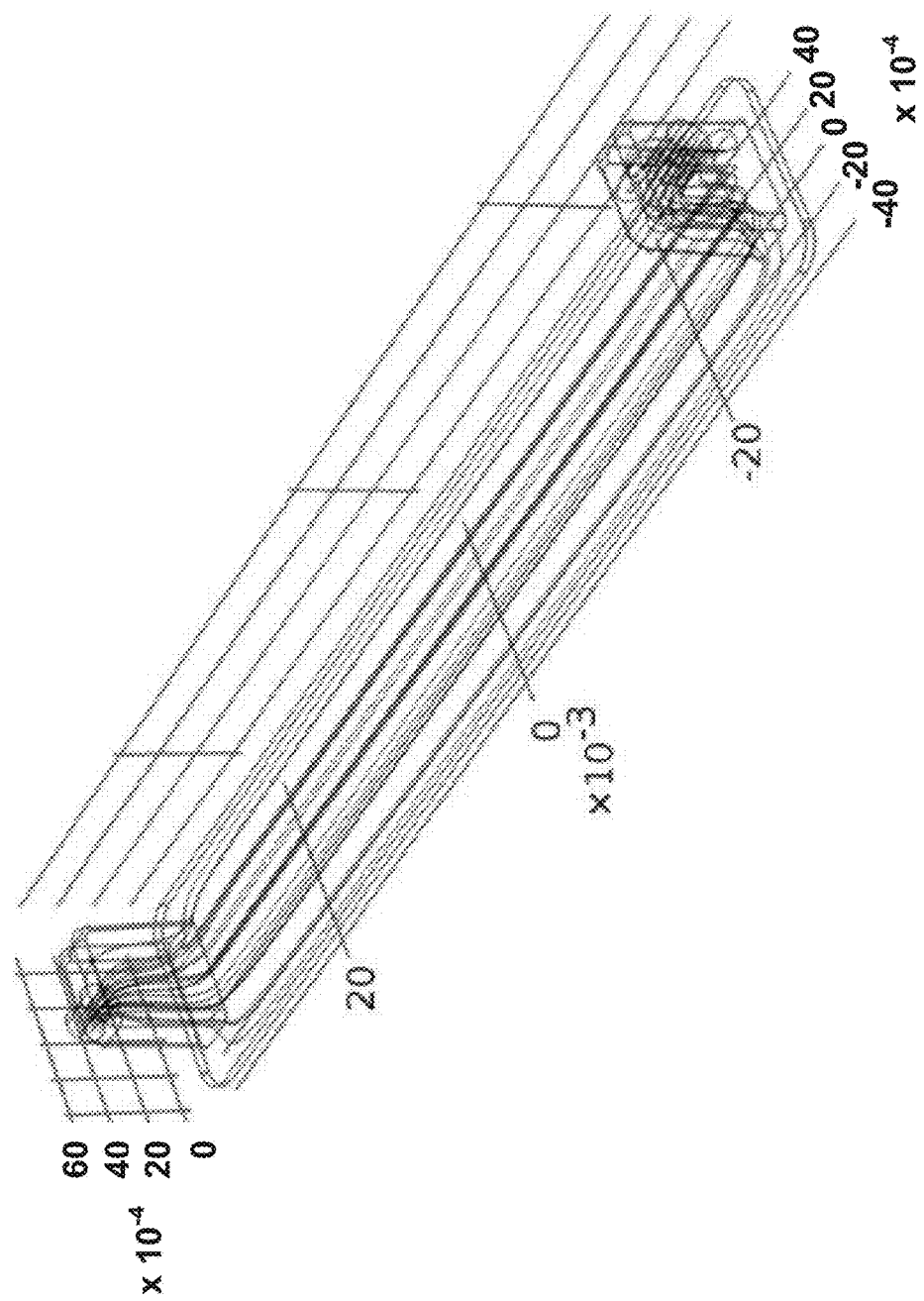
Figure 10D:
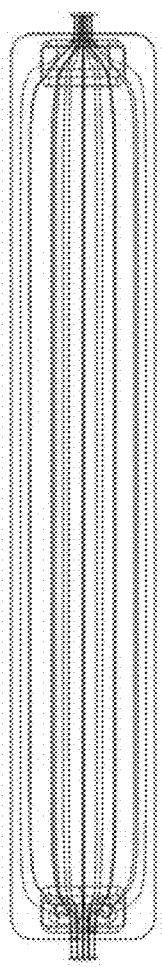

Referring now to FIGS. 9A and 9B, column position gridlines 902 and row position gridlines 904 are superimposed over inner panel 102 of the presently disclosed subject matter. Gridlines 902 and 904 intersect to define column/row positions 906 where the wells on a standard 96-well plate would occur. In some embodiments, each column/row position 906 of gridlines 902 and 904 corresponds to the center of a virtual well 908. Thus, with respect to top view window 114, approximately four virtual wells 908 of a 96-well plate can be encompassed through four column/row positions 906. Further, ports 108 are located in column/row positions 906, and are thus aligned with well positions of a standard 96 well plate. In accordance with an aspect of the presently disclosed subject matter, then, outer frame 104 defines a perimeter of the presently disclosed flow chamber 100 that is standardized to facilitate automated readout and handling of flow chamber 100. Accordingly, flow chamber 100 has overall dimensions of a standard 6, 12, 24, 48, 96, 384, or 1024 well multiwell plate and flow channel 404 is located in a position that corresponds to a column/row location of a standard 6, 12, 24, 48, 96, 384, or 1024 well multiwell plate. Further, referring back to FIG. 4, as seen by horizontal line 410 across the top of FIG. 4, the height of the outer frame 104 is also a standard height. Thus, again, in accordance with one aspect of the presently disclosed subject matter the whole device layout is designed to facilitate integration with robots, liquid handlers, and plate readers/high content screening microscopy systems. All of the features of flow chamber 100 fit into a package that is defined by the parameters required for automated handling (overall size, height and feature locations).

As can be seen in FIGS. 1-4 and 9, flow chamber 100 can comprise two or more flow channels 404. Indeed, flow chamber 100 can comprise in some embodiments two, in some embodiments three, in some embodiments four, in some embodiments five, in some embodiments six, in some embodiments seven, in some embodiments eight, and in some embodiments up to twelve or more flow channels 404. In such embodiments, each flow channel 404 can be individually located in a column/row position that corresponds to a different column/row position of a standard multiwell plate (e.g., a standard 6, 12, 24, 48, 96, 384, or 1024 well multiwell plate). In some embodiments, flow channel 404 is aligned with column/row positions on a standard 96 well plate and/or a standard 384 well plate.

In some embodiments, the inner panel, the outer frame, the one or more view windows, or any combination thereof are made from one or more non-birefringent and non-autofluorescent plastics. In some embodiments, the inner panel and the outer frame are produced by injection molding. In some embodiments, the overall dimensions of the flow chamber are consistent with ANSI/SBS well (e.g., plate standards that correspond to standard 6, 12, 24, 48, 96, 384, and/or 1024 well multiwell plates). In some embodiments, the flow chamber is provided as a preassembled, presterilized, liquid tight, and tissue culture ready device.

As presented in FIG. 10, an exemplary embodiment of the presently disclosed flow chamber generates and maintains parallel fluid streamlines along surface 304 and growth surface 408 within 30 µm of flow channel inlet/outlet 202 locations. Computational fluid dynamics simulations were performed using Comsol MULTIPHYSICS® Software v. 4.4 for a physiologically relevant arterial shear stress of 1.5 Pa at fluid viscosities or 0.8 (water) and 3.0 (blood) cP. The different viscosities result in differential fluid flow rates through the channel to achieve the target shear stress; a peak flow rate of 38.82 ml/min was used for the 0.8 cP case. These results indicate that the fluid dynamics in the channel are stable, and provide laminar parallel flow over a wide range of operating conditions. FIGS. 10A and 10B—streamlines for 0.8 cP fluid at 1.5 Pa. FIGS. 10C and 10D—streamlines for 3.0 cP at 1.5 Pa.

The presently disclosed flow chambers can be employed for culturing cells and/or tissues under exposure to fluid flow for the purpose of generating cells or tissues with a desired physiological phenotype that is related to developmental biology, cardiovascular disease, cancer, inflammation, and/or any other condition that cells and/or tissues from an organism may from time to time experience. Cells of interest can be attached to growth surface 408 of flow channel 404 and exposed to various user-defined fluid flow characteristics with or without treatment materials for a desired length of time.

For example, in some embodiments the presently disclosed flow chambers can be employed by introducing cells onto growth surface 408, then reducing or eliminating flow through flow channel 404 to allow for cell adhesion to growth surface 408. Once cells are adhered, fluid flow is ramped up to a flow rate of interest and held for a desired time period, with or without the introduction of treatment materials. Upon achievement of experimental goals, the induced properties of the cultured cells can be examined at the whole cell, protein, or nucleic acid level.

Cell types that can be tested using the flow chambers and methods of the presently disclosed subject matter include, but are not limited to, primary mammalian cells (e.g., endothelial cells, epithelial cells, smooth muscle cells, cardiomyocytes, chondrocytes, macrophages, and transformed cells), stem cells (e.g., embryonic stem cells, adult stem cells, and induced pluripotent stem cells), cell lines (e.g., cancer cells, immortalized cell lines, etc.), bacteria, yeast, and any other cell for which examination of growth responses and/or changes in biological activities under different flow conditions might be desired. In some embodiments, a pure culture of cells is employed, and in some embodiments combinations of different cell types are employed.

Growth surface 408 of flow channel 404 can be modified in various ways to influence the growth and/or attachment of deposited cells. Non-limiting examples of modifications to growth surface 408 include including addition of extracellular matrix components in a molecular layer or three-dimensional (3D) support (e.g., collagen, fibronectin, laminin, proteoglycans, and/or peptides), molecular layers or 3D supports made of other materials (e.g., hydrogels and/or polymers), chemical treatment, and/or other biological materials.

Materials and reagents can be added and removed through flow channel inlet/outlet 202 and/or through port 108. After growth surface 408 is prepared, in some embodiments cells and media can also be added flow channel inlet/outlet 202 and/or through port 108.

Cells cultured in flow channel 404 and exposed to fluid forces and/or chemical or biochemical treatment materials can be evaluated for biomarker expression using high-throughput analysis methods. Flow conditions and chemical or biochemical environments that are related to known characteristics of either healthy or diseased tissues may be chosen for these studies. By way of example and not limitation, expended culture medium can be removed from flow channel 404 via port 108 and the cells on growth surface 408 washed with appropriate buffer via ports 108. A lysis agent can be added to cells on growth surface 408 via port 108. After the cells lyse, cellular material can collected through port 108 (e.g., by suction via a pipette) and processed for nucleic acid analysis by microarrays or next-generation sequencing, protein analysis by immunoblot or mass spectroscopy, and/or other methods.

Cells growing on growth surface 408 can also be exposed to a set of desired flow conditions in flow channel 404 and then treated with various bioactive molecules (e.g., cytokines, chemokines, hormones, growth factors, etc.) and/or other chemical moieties (e.g., pharmaceutical compounds, contrast agents, organic compounds, inorganic compounds, etc.) to investigate how physiological responses to the bioactive molecules and/or chemical moieties are affected by various flow conditions. Cells can also be exposed to a set of desired flow conditions and then treated with molecular biology molecules and/or reagents (e.g., siRNA, shRNA, miRNA, DNA, plasmids, proteins, etc.) to determine how physiological responses to these molecules are affected by various flow conditions.

In some embodiments, cells are treated with biochemicals, chemical moieties, and/or molecular biology molecules and/or reagents prior to the application of flow. In some embodiments, cells are treated with biochemicals, chemical moieties, and/or molecular biology molecules and/or reagents after the application of flow. Outcomes are to determine how the flow conditions affect cell physiology and/or any other biologically relevant characteristic of the cells (including, but not limited to gene expression profiles) and/or how the treatment conditions interact with flow conditions to affect cell physiology. In some embodiments, a biologically relevant parameter observed for a cell and/or tissue growing in flow chamber 100 prior to the addition of a selected biochemical, chemical moiety, and/or molecular biology molecule and/or reagent under a given flow condition is compared to the same biologically relevant parameter observed for a cell and/or tissue growing in flow chamber 100 after the addition of a selected biochemical, chemical moiety, and/or molecular biology molecule and/or reagent. In some embodiments, a biologically relevant parameter observed for a cell and/or tissue growing in flow chamber 100 under a first flow condition is compared to the same biologically relevant parameter observed for a cell and/or tissue growing in flow chamber 100 under a second flow condition. In some embodiments, a selected biochemical, chemical moiety, and/or molecular biology molecule and/or reagent is added to a cell and/or tissue growing in flow chamber 100 before, during, or after the first flow condition is changed to the second flow condition.

Intact cells can be recovered from growth surface 408 by adding reagents, such as but not limited to, wash buffers, proteases (e.g., trypsin), or any other reagents that are generally employed to remove cells from growth supports or substrates, to flow channel 404 through port 108 on one end of flow channel 404 and removed through port 108 located on the other end of flow channel 404. Recovered cells can be analyzed by flow cytometry, microscopy, chemiluminescence, microarray, or other assays.

In some embodiments, in situ analysis is performed on fixed or unfixed cells present within flow channel 404. The expression of target molecules (e.g., polypeptides, phosphorylated polypeptides, nucleic acids, etc.) can be measured via labeling with appropriate labeling and/or detection reagents that can be applied to the cells. These labels can bind to the target molecules and provide optical, chemiluminescent, fluorescent, and/or radiological detection of the target molecules.

Single and/or pluralities of flow chamber 100 of the presently disclosed subject matter can be handled by automated (e.g., robotic moving of plates and automated liquid processing) or manual mechanisms.

Additionally, cell adhesion experiments can be performed using flow chamber 100 of the presently disclosed subject matter. By way of example and not limitation, leukocytes, bacteria, cancer cells, and/or other cells can be flowed over the surface of growth surface 408 and analyzed for adhesion to growth surface 408, which in some embodiments can already contain adherent cells and/or other surface modifications. Surface modifications include, but are not limited to addition of extracellular matrix molecules, ligands, and/or other biological and/or chemical moieties.

Particles, such as nanoparticles or larger entities, can also be flowed over growth surface 408 for determining binding of the nanoparticles or larger entities to an unmodified or modified growth surface 408 in the presence or absence of pre-deposited cells. Applications include but are not limited to cellular toxicity testing, binding kinetics, drug delivery, and cell targeting testing of nanoparticles, contrast agents, microbubbles, liposomes, and/or other particles.

The flow chambers of the presently disclosed subject matter can be employed in any method wherein examination of different responses of biological molecules, cells, tissues, and/or organs to different flow conditions is desired. By way of example and not limitation, the presently disclosed flow chambers can be employed for exposing biological molecules, cells, tissues, and/or organs to a set of desired flow conditions and then examining the same for flow and/or time dependent differences in relevant biological features and/or physiological properties.

Alternatively or in addition, biological molecules, cells, tissues, and/or organs can be exposed to a set of desired flow conditions and then exposed to with particular bioactive molecules (e.g., cytokines, chemokines, hormones, growth factors, etc.) and/or other chemical moieties (e.g., pharmaceutical compounds, organic compounds, inorganic compounds, etc.) to determine how physiological responses to the treatment conditions are affected by and/or otherwise respond to the flow conditions.

Additionally, biological molecules, cells, tissues, and/or organs can be exposed to a set of desired flow conditions and then treated with molecular biology molecules and/or reagents (e.g., siRNA, shRNA, miRNA, DNA, plasmids, proteins, etc.) to determine how physiological responses to the treatment conditions are affected by and/or otherwise respond to the flow conditions.

Derivatives of the analyses described above are also within the scope of the presently disclosed subject matter. For example, treatment with biochemicals, chemical moieties, and/or molecular biology molecules and/or reagents can be conducted prior to, during, and/or subsequent to the application of any particular flow condition, whether tested singularly or in combination. Potential readouts can include, but are not limited to determining how any particular treatment conditions (e.g., bioactive molecule exposure) can affect cell physiology in combination with a given flow exposure and/or how the treatment conditions interact with flow stimulation to affect cell physiology.

Furthermore, the analyses described herein above can also be conducted to compare any desired biological feature under any treatment and/or flow condition of wild type vs. mutant biomolecules, cells, tissues, and/or organs; biological molecules, cells, tissues, and/or organs derived from specific strains and/or genetically modified versions of any adherent cell type, either prokaryotic or eukaryotic; etc.

Possible endpoints for the methods of the subject matter described herein can be classified in two groups. In some embodiments, intact cells can be recovered for FACS, flow cytometry, and/or additional profiling/cell culture, as well as recovery of cell extracts for analysis of RNA, DNA, and/or or protein fractions. In some embodiments, intact cells can be recovered by adding appropriate reagents (e.g., wash buffers, trypsin/EDTA, etc.) to the flow channel through one port on top of the channel and removed by the other port. Similarly and in some embodiments, for cell extracts, appropriate wash and/or lysis buffers can be added through one port and removed through the other. In situ analyses can also be performed on fixed or unfixed cells within the flow channel. In some embodiments, appropriate buffers and/or reagents can also be added through one port on top of a flow channel and removed via the other. In some embodiments, instead of removing the cells or cell extracts, exemplary studies can measure the expression of target molecules via labels contained in the reagents applied to the cells. These labels can bind with the target molecules and facilitate optical and/or radiological detection.

In some embodiments the flow chambers of the presently disclosed subject matter can be handled by automated devices (e.g., robotic moving of plates and automated liquid processing) and/or manually.

An additional assay that can be performed using the flow chambers and methods of the presently disclosed subject matter is a cell adhesion experiment. By way of example and not limitation, leukocytes, bacteria, cancer cells, and/or other cells can be flowed over the surface of the presently disclosed flow device and analyzed for their adhesion to the surface. In some embodiments, the surface itself can contain adherent cells and/or be a standard and/or modified surface. Surface modifications can include, but are not limited to addition of extracellular matrix molecules, ligands, and/or other biological and/or chemical moieties.

Particle binding studies can also be performed. Particles, including but not limited to nanoparticles, microparticles, and larger entities, can be flowed over the flow device surface for determining binding to unmodified and/or modified surfaces in the absence or presence of cells. In some embodiments, cellular toxicity testing, binding kinetics, drug delivery, and cell targeting testing of nanoparticles, contrast agents, microbubbles, liposomes, and other particles can be performed.

Flow-induced phenotypic alterations can also be tested. Cells and/or tissues can be grown and/or exposed to flow in a flow chamber of the presently disclosed subject matter for the purpose of generating cells or tissues with a physiological or pathological phenotype related to developmental biology, cardiovascular disease, cancer, inflammation, bones, joints, lymph, lungs or other cells or tissues from an organism. Cells and/or tissues can be mammalian or non-mammalian cells including, but not limited to primary mammalian cells (e.g., endothelial cells, epithelial cells, smooth muscle cells, cardiomyocytes, chondrocytes, macrophages, transformed cells), stem cells (e.g., embryonic stem cells, adult stem cells, induced pluripotent stem cells), cell lines (cancer cells, immortalized cell lines, etc.), bacteria, yeast, or other cells. bacterial cells and biofilms, yeast, and/or cells and/or tissues derived from worms, zebrafish, or other organisms. In some embodiments, pure cultures or combinations of cell types can be used.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Biomarker Analysis of Fluid Flow Conditioned Cells

Gene expression differences under two different shear stress conditions were tested in Human Aortic Endothelial Cells, using a flow chamber device.

Table 1 shows the number of genes changed between Human Aortic Endothelial Cells exposed to 1.0 Pa wall shear stress for 20 hours as compared to cells exposed to no flow. Cells were cultured on a collagen I-coated growth surface under static conditions (no flow) until confluency was reached. Cells were then either exposed to fluid flow in a flow chamber at 0.2 or 1.0 Pa for 20 hours, or left in static culture for the same amount of time. At 20 hours, RNA was isolated from the cells using an Ambion MIRVANA™ RNA isolation kit (Life Technologies, Foster City Calif., United States of America) and processed for analysis on Affymetrix PRIMEVIEW™ arrays (Affymetrix, Inc., Santa Clara, Calif., United States of America). Three experiments were performed for each condition, providing replicates for microarray analysis.

Table 1 shows the number of genes that were significantly different between pairs of conditions. For cells exposed to 0.2 Pa shear stress, there were 162 genes that significantly changed expression compared to cells not exposed to fluid flow. A similar number of genes were changed for cells exposed to 1.0 Pa shear stress compared to cells not exposed to flow. However, there were 234 genes changed between cells exposed to 0.2 Pa and 1.0 Pa shear stress. These results indicate that both the presence of flow and the average shear stress magnitude provided each significantly influenced cell physiology. These findings of differentially-expressed genes establish that flow based assays can provide important information on the physiological state of cells that is not available from statically conducted experiments. For experimental work that targets in vivo physiology, flow assays can provide a more relevant model than static experiments to study aspects of human or animal health and disease. The genes identified in the experiments described herein can be further characterized and tested as targets for human therapeutic modulation and/or diagnostics.

TABLE 1

| Gene Expression Differences Between Different Shear Stress Conditions | | |
|---|---|---|
| Condition 1 | Condition 2 | No. of Genes Changed |
| No Shear | 0.2 Pa | 162 |
|  | 1.0 Pa | 158 |
| 0.2 Pa | 1.0 Pa | 234 |

Example 2

Drug Treatment of Fluid Flow Preconditioned and Statically Cultured Cells

Gene expression differences in Human Aortic Endothelial Cells were also tested under different shear stress conditions, using a flow chamber device, in the presence or absence of the PI3K/Akt and mTOR inhibitor PI-103 (3-[4-(4-morpholinyl)pyrido[3',2':4,5]furo[3,2-d]pyrimidin-2-yl]-phenol); CAS No. 371935-74-9) at a concentration of 100 nM.

Cells were grown on a collagen-I coated growth surface and treated with 100 nM PI-103 in the presence of flow. For the 4 hour time point, cells were exposed to fluid flow for 16 hours and treated with PI-103 for the last 4 hours in the presence of flow. Cells were also treated with PI-103 for the entire duration of flow (20 hours). Data was generated using RNA extracted as described in Example 1, and analyzed on Affymetrix PRIMEVIEW™ arrays (Affymetrix, Inc.,). Three experiments were performed for each condition, providing replicates for microarray analysis.

Table 2 shows the number of genes that were significantly different between pairs of conditions. Cells grown only under static conditions and treated with 4 hours of PI-103 had 130 genes change in comparison to non-treated cells under static conditions. Cells exposed to PI-103 under flow conditions changed a larger number of genes compared to non-treated cells under the same flow conditions (see Table 2); drug treatment (4 hr) at the low flow condition (0.2 Pa) changed 830 genes while drug treatment (4 hr) at the high flow condition (1.0 Pa) changed 1563 genes. Treatment of cells with drug for 20 hours resulted in a smaller number of genes changed for cells exposed to flow (see Table 2). These results show the level of flow exposure (0, 0.2 Pa, or 1.0 Pa) can modify endothelial gene expression in response to PI-103 treatment, and indicates that cell culture environment is an essential aspect of experimental design. PI-103 results were highly divergent between statically cultured cells and both flow conditions, indicating that static culture based assays may be inefficient for predicting how pharmaceutical compounds will interact with living bodies. By establishing flow based assays that mimic the flow properties in target tissues, a more relevant physiological environment can be provided for early stage pharmaceutical experiments.

TABLE 2

Gene Expression Differences Between Different Shear Stress Conditions and Drug Exposure Times

| Condition 1 | Condition 2[a] | No. of Genes Changed |
| --- | --- | --- |
| No Shear | 4 hr | 130 |
|  | 20 hr | 159 |
| 0.2 Pa | 4 hr | 830 |
|  | 20 hr | 113 |
| 1.0 Pa | 4 hr | 1563 |
|  | 20 hr | 119 |

[a]Condition 2 relates to drug exposure time

Example 3

Identification of Protein Species' Interaction Upon Flow Stimulation

Human Aortic Endothelial Cells were cultured on a collagen I-coated growth surface under static conditions (no flow) until confluency was reached. Cells were then either exposed to fluid flow in a flow chamber device at 1.0 Pa for 20 hours, or left in static culture for the same amount of time. At the 20 hour time point, both sets of cells were washed well with phosphate buffered saline (PBS), and then fixed for 20 minutes at room temperature with 4% p-formaldehyde in PBS. Following fixation, cells were permeabilized with 0.1% TRITON™ X-100 in PBS at room temperature for 15 minutes. Once permeabilized, cells were well washed again with PBS and then processed according to the instructions of the DUOLINK® II Kit from Olink Bioscience (Uppsala, Sweden). The DUOLINK®II Kit identifies protein-protein interactions based upon a technique known as proximity ligation assay. Primary antibodies for the target species of Smad2 and Integrin Linked Kinase 1 (ILK) were used at the manufacturer's recommended dilution for immunofluorescence applications.

Figures 11A, 11B, 11C, 11D, 11E, 11F:
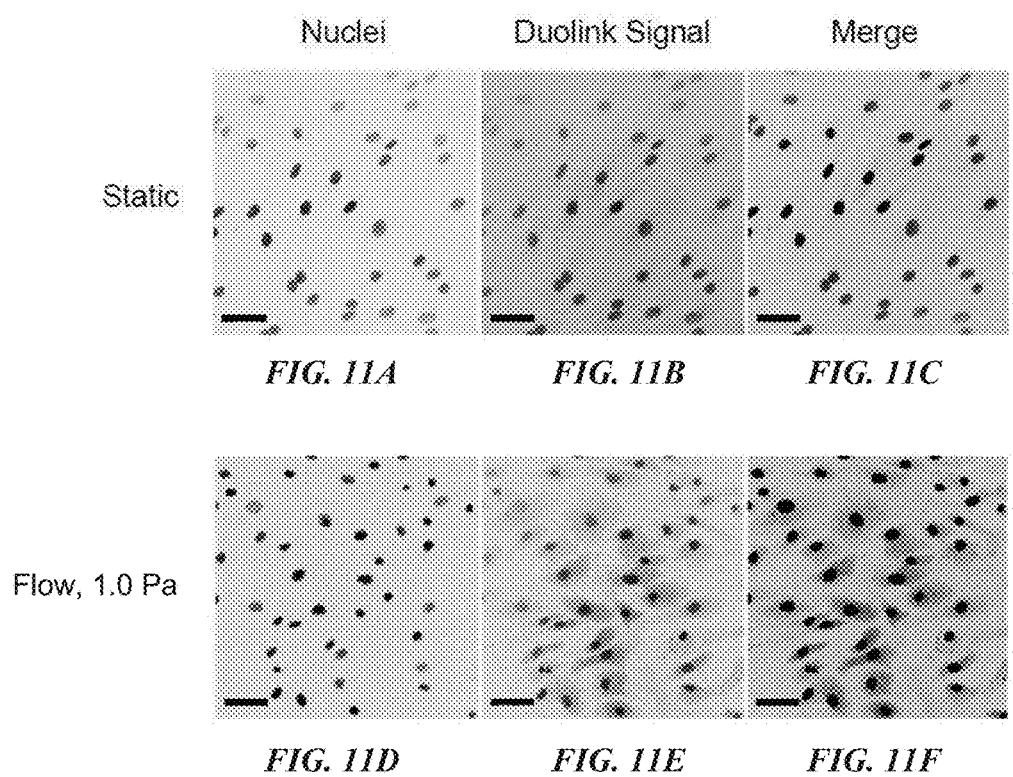
FIGS. 11A-11F are a series of photomicrographs presenting the results of a DUOLINK® study examining the association of two proteins, Smad2 and ILK, under both static and flow conditions. Human Aortic Endothelial Cells were grown to confluence before initiating flow at 1.0 Pa for 20 hours, or maintaining static conditions for the same time. The solid bar in the lower left corner of each panel represents 50 µm.

FIGS. 11A-11E present six (6) confocal laser scanning microscopy panels, three (3) for each condition. FIGS. 11A and 11D show nuclei stained with DAPI, FIGS. 11B and 11E show DUOLINK® signal (indicating protein-protein interaction), and FIGS. 11C and 11F show the nuclei and DUOLINK® signal merged. As evident from FIGS. 11A-11F, statically cultured cells showed essentially no interactions between Smad2 and ILK. However, cells experiencing 20 hours of flow stimulation at 1 Pa showed significant interactions between the two proteins.

These experiments demonstrated the ability to employ flow versus static assays to study cellular based protein activation and interaction phenomena, especially when the targeted interactions might exist in vivo. Additionally, the use of microscopy as an assay technique for flow chamber experiments was demonstrated. While not wishing to be bound by any particular theory of operation, it is possible that had these experiments been conducted only in statically cultured cells, the interactions between Smad2 and ILK would likely have gone unobserved.

Example 4

In Situ Detection of Multiple Fluorescently Labeled Proteins by Microscopy

FIG. 12 presents representative microscopy images of statically grown human aortic endothelial cells that were stained for total levels of Akt and F-actin. In this experiment, the ability to detect and distinguish multiple fluorescent signals through a relatively thick (1.2 mm) polystyrene substrate was investigated. Accomplishment of this imaging task demonstrated the utility of performing optical assays in flow chambers produced from polystyrene and other plastic materials. Importantly, three fluorophores with distinct excitation and emission characteristics were employed, sequentially imaged on an Olympus FV1000 laser scanning confocal microscope, and reconstructed into clear composite images. Each individual channel was capable of being individually examined for expression characteristics of the target protein/structure.

To accomplish this experiment, endothelial cells were cultured in three (3) T-25 flasks until confluent with Lonza EGM-2 growth media (Lonza Inc., Allendale, N.J., United States of America) and then rinsed twice with 5 ml PBS and fixed with 2 ml 4% p-formaldehyde in PBS for 15 minutes at room temperature. Following fixation, the cells were rinsed twice more, and then washed for 5 minutes in 5 ml PBS. A solution of 0.1% TRITON™ X-100 in PBS was then added to the cells for 15 minutes at room temperature to permeabilize the cell membrane, and the PBS rinse/wash steps repeated. 5 ml of 5% rabbit serum in PBS was then added to the cells, and they were allowed to block 6 hours at 4° C. with gentle agitation. A second blocking step using 3% bovine serum albumin (BSA) in PBS was performed for 1 hour at room temperature, and then a primary rabbit antibody to total Akt (Cell Signaling Technology, Danvers, Mass., United States of America) was added at a dilution of 1:500 in a solution of 3% BSA in PBS. Primary antibody was allowed to incubate overnight at 4° C. with gentle agitation. Rinse/wash steps were repeated with 3% BSA in PBS, and then a secondary antibody conjugated with ALEXA FLUOR® 555 (Life Technologies, Foster City, Calif., United States of America) was incubated with the cells for 1 hour at room temperature. Rinse/wash steps were repeated with PBS, and then a solution of Hoechst 33258 (Life Technologies, Foster City, Calif., United States of America) and FITC-labeled Phalloidin (Life Technologies, Foster City, Calif., United States of America) in PBS were added at 1 μg/ml each. These components were incubated with the cells for 10 minutes at room temperature, and then rinse/wash steps repeated. A fresh 2 ml volume of PBS was added to the cells, and each flask was imaged on the Olympus FV1000 microscope.

Discussion of the Examples

As set forth herein, the presently disclosed flow chambers and methods can be employed for assaying a biological feature of cultured cells and/or tissues, or even isolated biologically interesting molecules including, but not limited to nucleic acids, peptides, polypeptides, polysaccharides, etc. As used herein, the phrase "biological feature" refers to any characteristic of a biomolecule that might be of interest and/or that might be altered by different flow conditions. In some embodiments, a biological feature comprises a growth rate, an apoptosis or death rate, a morphology, and/or an expression profile of one or more gene products in a cultured cell and/or tissue before, after, and/or during application of one or more different flow conditions.

Additionally, the presently disclosed flow chambers and methods can be employed in network analysis to analyze, for example, gene expression and/or protein data under different flow conditions and correlate data derived therefrom with any other gene expression and/or protein expression data from any other source thereby derived to identify biological pathways that are likely to be involved in the physiology created in a given flow chamber experiment and/or flow condition. This can be a powerful technique that can be employed for novel biomarker discovery and/or novel drug target discovery based upon relatively simple flow experiments employing the presently disclosed flow chambers and/or methods. These data can be acquired in a manner similar to that described herein above in the EXAMPLES, such as by running microarrays on RNA extracted from flow chamber cultivated/stimulated cells. Such analyses can employ specialized software and can be related to gene expression and/or protein expression and/or phosphorylation data, among other possible readouts.

Accordingly, the features of the presently disclosed flow chambers are not available in an existing technology that supports both manual and automated performance and analysis of flow based cellular assays.

REFERENCES

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

Anderson et al. (2006) The imperative for controlled mechanical stresses in unraveling cellular mechanisms of mechanotransduction. *BioMed Eng OnLine* 5:27.

Brown & Larson (2001) Improvements to parallel plate flow chambers to reduce reagent and cellular requirements. *BMC Immunol* 2:9.

Buchanan et al. (1999) Relation between non-uniform hemodynamics and sites of altered permeability and lesion growth at the rabbit aorto-celiac junction. *Atherosclerosis* 143:27-40.

Burns & DePaola (2005) Flow-conditioned HUVECs support clustered leukocyte adhesion by coexpressing ICAM-1 and E-selectin. *Am J Physiol Heart Circ Physiol* 288:H194-H204.

Chatzizisis et al. (2007) Role of endothelial shear stress in the natural history of coronary atherosclerosis and vascular remodeling: molecular, cellular, and vascular behavior. *J Am Col Cardiol* 49:2379-2393.

Chiu et al. (2007) Mechanisms of induction of endothelial cell E-selectin expression by smooth muscle cells and its inhibition by shear stress. *Blood* 110:519-528, 2007.

Dai et al. (2004) Distinct endothelial phenotypes evoked by arterial waveforms derived from atherosclerosis-susceptible and -resistant regions of human vasculature. *Proc Natl Acad Sci USA*. 101:14871-14876, 2004.

Dekker et al. (2002) Prolonged fluid shear stress induces a distinct set of endothelial cell genes, most specifically lung Kruppel-like factor (LKLF2). *Blood* 100:1689-1698.

Duan et al. (2010) Shear stress induced changes of membrane transporter localization and expression in mouse proximal tubule cells. *Proc Natl Acad Sci USA* 107: 21860-21865.

Essig & Friedlander (2003) Tubular shear stress and phenotype of renal proximal tubular cells. *J Am Soc Nephrol* 14:S33-S35.

Frangos et al. (1985) Flow effects on prostacyclin production by cultured human endothelial cells. *Science* 227: 1477-1479, 1985.

LaMack et al. (2005) Interaction of wall shear stress magnitude and gradient in the prediction of arterial macromolecular permeability. *Annals Biomed Eng* 33:457-464.

McCann et al. (2005) Non-uniform flow behavior in a parallel plate flow chamber alters endothelial cell responses. *Ann Biomed Eng* 33:328-336.

McKinney et al. (2006) Normal and shear stresses influence the spatial distribution of intracellular adhesion molecule-1 expression in human umbilical vein endothelial cells exposed to sudden expansion flow. *J Biomech* 39:806-817.

McNeish (2004) Embryonic stem cells in drug discovery. *Nature Rev Drug Disc* 3:70-80.

Nauman et al. (1999) Quantitative assessment of steady and pulsatile flow fields in a parallel plate flow chamber. *Ann Biomed Eng* 27:194-199.

Rinker et al. (2001) Effect of contact time and force on monocyte adhesion to vascular endothelium. *Biophys J* 80:1722-1732.

Shah et al. (1997) Liver sinusoidal endothelial cells are responsible for nitric oxide modulation of resistance in the hepatic sinusoids. *J Clin Invest* 100:2923-2930.

Sheikh et al. (2005) Differing mechanisms of leukocyte recruitment and sensitivity to conditioning by shear stress for endothelial cells treated with tumour necrosis factor-α or interleukin-1β. *Br J Pharmacol* 145:1052-1061.

Shepherd et al. (2009) Long term shear stress leads to increased phosphorylation of multiple MAPK species in cultured human aortic endothelial cells. *Biorheology* 46:529-538.

Shepherd et al. (2011) Flow-dependent Smad2 phosphorylation and TGIF nuclear localization in human aortic endothelial cells. *Am J Physiol Heart Circ Physiol* 301: H98-H107.

Tsai et al. (2007) Laminar flow attenuates interferon-induced inflammatory responses in endothelial cells. *Cardiovasc Res* 74:497-505.

Urbich et al. (2001) Upregulation of TRAF-3 by shear stress blocks CD40-mediated endothelial activation. *J Clin Invest* 108:1451-1458.

Wasserman & Topper (2004) Adaptation of the endothelium to fluid flow: in vitro analyses of gene expression and in vivo implications. *Vasc Med* 9:35-45.

Yamamoto et al. (2005) Fluid shear stress induces differentiation of Flk-1-positive embryonic stem cells into vascular endothelial cells in vitro. *Am J Physiol Heart Circ Physiol* 288:H1915-H1924.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for assaying or identifying a biological feature of a cultured cell or tissue, the method comprising:
   (a) growing a cultured cell or tissue on a growth surface present in a flow chamber comprising an outer frame adapted to receive an inner panel to form at least one flow channel there between, wherein:
     (i) the inner panel comprises:
       (1) a lower surface comprising one or more recesses bounded by one or more grooves, each recess further comprising both a flow channel inlet/outlet and a port at each end, wherein each flow channel inlet/outlet is adapted to receive a septum and each port is adapted to releasably receive a plug to provide a liquid-proof seal to the at least one flow channel, optionally wherein the ports are adapted to be resealable; and
       (2) an upper surface comprising one or more septum holders each comprising a septum, wherein each septum holder is aligned with a flow channel inlet/outlet;
     (ii) an outer frame that defines a perimeter of the flow chamber, wherein the outer frame comprises one or more welding ribs on its inner horizontal surface and one or more pairs of fluidics holes on one or more opposing vertical surfaces; and
     (iii) when the outer frame receives the inner panel, the one or more welding ribs fit into the one or more grooves to form the at least one flow channel and the one or more septum holders align each septum with a fluidics hole;
   (b) applying a first flow condition to the cultured cell or tissue; and
   (c) assaying or identifying a biological feature of the cultured cell or tissue under the first flow condition to produce a first analysis of the biological feature of the cultured cell or tissue under the first flow condition.

2. The method of claim 1, wherein the biological feature comprises a growth rate, an apoptosis or death rate, a morphology, a physiological parameter, and/or an expression profile of one or more gene products in the cultured cell or tissue before, after, and/or during application of the first flow condition.

3. The method of claim 2, wherein the assaying or identifying comprises generating a gene expression profile of one or more genes in the cultured cell or tissue before, after, and/or during application of the first flow condition.

4. The method of claim 1, further comprising applying a second flow condition to the cultured cell or tissue after application of the first flow condition.

5. The method of claim 4, wherein the first flow condition and the second flow condition are different.

6. The method of claim 5, wherein the first flow condition or the second flow condition comprises a static flow condition.

7. The method of claim 4, further comprising assaying the biological feature of the cultured cell or tissue subsequent to and/or while applying the second flow condition to produce a second analysis of the biological feature of the cultured cell or tissue under the second flow condition.

8. The method of claim 7, wherein the biological feature comprises gene expression levels of one or more genes in the cultured cell or tissue.

9. The method of claim 7, further comprising comparing the first analysis to the second analysis in order to identify differences in a response of the cultured cell or tissue to the first flow condition as compared to the second flow condition.

10. The method of claim 9, wherein the biological feature comprises gene expression levels of one or more genes in the cultured cell or tissue and the comparing step identifies at least one gene for which expression differs in under the first flow condition as compared to the second flow condition by at least two-fold.

11. The method of claim 1, wherein the outer frame comprises a surface upon which cells can be grown in culture.

12. The method of claim 1, wherein the flow chamber has overall dimensions of a standard 6, 12, 24, 48, 96, 384, or 1024 well multiwell plate and the at least one flow channel is located in a position that corresponds to a column location of the standard 6, 12, 24, 48, 96, 384, or 1024 well multiwell plate and/or the one or more ports are positioned in locations aligned with well positions of the standard 6, 12, 24, 48, 96, 384, or 1024 well multiwell plate.

13. The method of claim 12, comprising two, three, four, five, six, seven, eight, or up to 12 flow channels, each of which is individually located in a column position that corresponds to a different column location of the standard 6, 12, 24, 48, 96, 384, or 1024 well multiwell plate.

14. The method of claim 1, wherein the at least one flow channel has dimensions of between about 5 and 80 mm long by about 1 and 20 mm wide by about 0.025 and 2.5 mm high.

15. The method of claim 1, wherein the at least one flow channel is characterized by one or more gaps, obstacles, and/or other modifications designed to create one or more variable fluid dynamic conditions within the at least one flow channel.

16. The method of claim 1, wherein the at least one flow channel has an increasing flow channel height along at least a portion of its length or is chemically and/or physically treated and/or is functionalized by reactive groups and/or by macromolecules.

17. The method of claim 1, wherein at least one of the one or more ports comprises fitted therein a polymer plug, optionally a gas permeable plug.

18. The method of claim 1, wherein the outer frame comprises a skirt defining a perimeter and welding ribs positioned along the bottom of the flow chamber.

19. The method of claim 18, further comprising one or more viewing windows positioned within the perimeter defined by the skirt and between the welding ribs.

20. The method of claim 1, wherein the outer frame:
   (i) is adapted to seal the septum in its corresponding inlet/outlet opening; and
   (ii) comprises one or more holes to access the septum for fluidics connections.

21. The method of claim 1, wherein the inner panel, the outer frame, or both comprise one or more view windows through which the at least one flow channel or a cell growing thereupon can be observed.

22. The method of claim 21, wherein the inner panel, the outer frame, the one or more view windows, or any combination thereof are made from one or more plastics that are non-birefringent, non-auto-fluorescent, or both.

23. The method of claim 1, further comprising at least a first liquid reservoir that is in fluid communication with the at least one flow channel via a first line attached to the first inlet/outlet opening.

24. The method of claim 1, wherein the flow chamber further comprises one or more contact points adapted to facilitate interaction of the flow chamber with an automated plate handling apparatus, a multiwell plate reader, an automated microscopy system or any combination thereof.

25. The method of claim 7, wherein the cultured cell or tissue is contacted with one or more bioactive molecules and/or other chemical moieties before, during, and/or after application of the first flow condition.

26. A method for assaying or identifying a biological feature of a cultured cell or tissue, the method comprising:
(a) growing a cultured cell or tissue on a growth surface present in a flow chamber comprising an outer frame adapted to receive an inner panel to form at least one flow channel there between, wherein:
  (i) the inner panel comprises:
    (1) a lower surface comprising one or more recesses bounded by one or more grooves, each recess further comprising both a flow channel inlet/outlet and a port at each end, wherein each flow channel inlet/outlet is adapted to receive a septum and each port is adapted to releasably receive a plug to provide a liquid-proof seal to the at least one flow channel, optionally wherein the ports are adapted to be resealable; and
    (2) an upper surface comprising one or more septum holders each comprising a septum, wherein each septum holder is aligned with a flow channel inlet/outlet;
  (ii) an outer frame that defines a perimeter of the flow chamber, wherein the outer frame comprises one or more welding ribs on its inner horizontal surface and one or more pairs of fluidics holes on one or more opposing vertical surfaces; and
  (iii) when the outer frame receives the inner panel, the one or more welding ribs fit into the one or more grooves to form the at least one flow channel and the one or more septum holders align each septum with a fluidics hole;
and further wherein:
  (iv) the outer frame has a footprint equivalent to that of a standard 6, 12, 24, 48, 96, 384, or 1024 well multiwell plate;
  (v) each of the at least one flow channels is located in a position that corresponds to a column location of the standard 6, 12, 24, 48, 96, 384, or 1024 well multiwell plate;
  (vi) each of the at least one flow channels comprises a plurality of virtual wells, each virtual well located in a position that corresponds to a well location of the standard 6, 12, 24, 48, 96, 384, or 1024 well multiwell plate; and
  (vii) when the outer frame receives the inner panel, the one or more welding ribs fit into the one or more grooves to form the at least one flow channel and the one or more septum holders align each septum with a fluidics hole;
(b) applying a first flow condition to the cultured cell or tissue; and
(c) assaying a biological feature of the cultured cell or tissue under the first flow condition to produce a first analysis of the biological feature of the cultured cell or tissue under the first flow condition.

27. The method of claim 26, further comprising applying a second flow condition to the cultured cell or tissue after application of the first flow condition.

28. The method of claim 27, wherein the first flow condition and the second flow condition are different.

29. The method of claim 27, further comprising assaying the biological feature of the cultured cell or tissue subsequent to and/or while applying the second flow condition to produce a second analysis of the biological feature of the cultured cell or tissue under the second flow condition.

30. The method of claim 29, wherein the cultured cell or tissue is contacted with one or more bioactive molecules and/or other chemical moieties after application of the first flow condition.

31. The method of claim 29, wherein the first flow condition or the second flow condition comprises a static flow condition.

* * * * *